(12) United States Patent
Tearney et al.

(10) Patent No.: US 10,288,868 B2
(45) Date of Patent: May 14, 2019

(54) OPTICAL PROBE, LIGHT INTENSITY DETECTION, IMAGING METHOD AND SYSTEM

(71) Applicants: CANON U.S.A., INC., Melville, NY (US); THE GENERAL HOSPITAL CORPORATION, Boston, MA (US)

(72) Inventors: Guillermo J. Tearney, Cambridge, MA (US); Dongkyun Kang, Somerville, MA (US); Mitsuhiro Ikuta, Cambridge, MA (US); Kenji Yamazoe, Tochigi (JP); Anderson Thi Mach, Cambridge, MA (US); Jacob Schieffelin Brauer, Cambridge, MA (US)

(73) Assignees: CANON U.S.A., INC., Melville, NY (US); THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 15/115,079

(22) PCT Filed: Jan. 30, 2015

(86) PCT No.: PCT/US2015/013816
§ 371 (c)(1),
(2) Date: Jul. 28, 2016

(87) PCT Pub. No.: WO2015/116951
PCT Pub. Date: Aug. 6, 2015

(65) Prior Publication Data
US 2016/0341951 A1    Nov. 24, 2016

Related U.S. Application Data

(60) Provisional application No. 61/934,486, filed on Jan. 31, 2014.

(51) Int. Cl.
*G02B 23/24* (2006.01)
*G02B 26/10* (2006.01)
(Continued)

(52) U.S. Cl.
CPC ...... *G02B 23/2453* (2013.01); *A61B 1/00009* (2013.01); *A61B 1/00096* (2013.01);
(Continued)

(58) Field of Classification Search
CPC ............ G02B 23/2453; G02B 23/2423; G02B 26/103; G02B 23/2469; G02B 27/1086;
(Continued)

(56) References Cited

U.S. PATENT DOCUMENTS 3,976,360 A    8/1976  Schroder
4,074,306 A    2/1978  Kakinuma et al.
(Continued)

FOREIGN PATENT DOCUMENTS

CN    102967365 A    3/2013
JP    2011-527930 A    11/2011
(Continued)

OTHER PUBLICATIONS

Zeidan, A., et al., "Miniature forward-viewing spectrally encoded endoscopic probe", Optics Express, Aug. 15, 2014, pp. 4871-4874, vol. 39, vol. 16.
(Continued)

*Primary Examiner* — Ryan A Lepisto
*Assistant Examiner* — Erin D Chiem
(74) *Attorney, Agent, or Firm* — Canon USA Inc., IP Division

(57) ABSTRACT

Exemplary apparatus, systems, methods of making, and methods of using a configuration in an optical arrangement for forward viewing spectrally encoded endoscopy (SEE) probe can be provided. For example, the probe can comprise
(Continued)

a light focusing component, a light guiding component, a light reflecting component, and a grating component.

28 Claims, 15 Drawing Sheets

(51) Int. Cl.
| | |
|---|---|
| A61B 1/00 | (2006.01) |
| A61B 1/04 | (2006.01) |
| A61B 1/06 | (2006.01) |
| A61B 1/07 | (2006.01) |
| H04N 5/225 | (2006.01) |
| G02B 27/10 | (2006.01) |
| G02B 27/42 | (2006.01) |
| G02B 23/02 | (2006.01) |
| H04N 9/07 | (2006.01) |
| G02B 23/26 | (2006.01) |
| G02B 23/00 | (2006.01) |
| G02B 3/00 | (2006.01) |

(52) U.S. Cl.
CPC ............ *A61B 1/00172* (2013.01); *A61B 1/04* (2013.01); *A61B 1/0661* (2013.01); *A61B 1/07* (2013.01); *G02B 3/0087* (2013.01); *G02B 23/02* (2013.01); *G02B 23/243* (2013.01); *G02B 23/2423* (2013.01); *G02B 23/2469* (2013.01); *G02B 23/26* (2013.01); *G02B 26/103* (2013.01); *G02B 27/1086* (2013.01); *G02B 27/425* (2013.01); *H04N 5/2256* (2013.01); *H04N 9/07* (2013.01); *H04N 2005/2255* (2013.01)

(58) Field of Classification Search
CPC ...... G02B 27/425; G02B 23/02; G02B 23/26; G02B 3/0087; G02B 23/243; A61B 1/00009; A61B 1/04; A61B 1/0661; A61B 1/07; A61B 1/00096; A61B 1/00172; H04N 5/2256; H04N 9/07; H04N 2005/2255
See application file for complete search history.

(56) References Cited

U.S. PATENT DOCUMENTS

| | | | |
|---|---|---|---|
| 4,264,127 | A | 4/1981 | Schumacher et al. |
| 5,565,983 | A | 10/1996 | Barnard |
| 5,909,529 | A | 6/1999 | Bhagavatula |
| 6,341,036 | B1 | 1/2002 | Tearney et al. |
| 6,485,413 | B1 | 11/2002 | Boppart et al. |
| 6,661,513 | B1 | 12/2003 | Granger |
| 6,831,781 | B2 | 12/2004 | Tearney et al. |
| 6,858,859 | B2 | 2/2005 | Kusunose |
| 7,003,196 | B2 | 2/2006 | Ghiron |
| 7,061,673 | B2 | 6/2006 | Mizuno |
| 7,489,713 | B2 | 2/2009 | Chong |
| 7,495,762 | B2 | 2/2009 | Wang |
| 7,796,270 | B2 | 9/2010 | Yelin et al. |
| 7,843,572 | B2 | 11/2010 | Tearney et al. |
| 7,859,679 | B2 | 12/2010 | Bouma et al. |
| 8,045,177 | B2 | 10/2011 | Tearney et al. |
| 8,145,018 | B2 | 3/2012 | Shishkov |
| 8,203,708 | B2 | 6/2012 | Lee et al. |
| 8,289,522 | B2 | 10/2012 | Tearney |
| 8,780,176 | B2 | 7/2014 | Yelin |
| 8,804,133 | B2 | 8/2014 | Yelin et al. |
| 8,812,087 | B2 | 8/2014 | Yelin et al. |
| 8,818,149 | B2 | 8/2014 | Shishkov et al. |
| 8,838,213 | B2 | 9/2014 | Tearney et al. |
| 9,254,089 | B2 | 2/2016 | Tearney et al. |
| 2002/0114566 | A1 | 8/2002 | Fairchild et al. |
| 2002/0145815 | A1 | 10/2002 | Moriyama et al. |
| 2003/0027328 | A1 | 2/2003 | Cunningham et al. |
| 2003/0142934 | A1 | 7/2003 | Pan et al. |
| 2004/0147810 | A1 | 7/2004 | Mizuno |
| 2004/0174529 | A1 | 9/2004 | Maznev et al. |
| 2005/0155704 | A1 | 7/2005 | Yokajty et al. |
| 2007/0188855 | A1 | 8/2007 | Shishkov et al. |
| 2007/0233396 | A1 | 10/2007 | Tearney et al. |
| 2008/0013960 | A1 | 1/2008 | Tearney et al. |
| 2008/0097225 | A1 | 4/2008 | Tearney et al. |
| 2009/0141360 | A1 | 6/2009 | Koyama |
| 2010/0210937 | A1 | 8/2010 | Tearney et al. |
| 2010/0317975 | A1 | 12/2010 | Yelin |
| 2011/0237892 | A1 | 9/2011 | Tearney et al. |
| 2011/0275899 | A1 | 11/2011 | Tearney et al. |
| 2012/0112094 | A1 | 5/2012 | Kao et al. |
| 2012/0328241 | A1 | 12/2012 | Shishkov et al. |
| 2013/0012771 | A1 | 1/2013 | Robertson |
| 2013/0331709 | A1 | 12/2013 | Le et al. |
| 2014/0221747 | A1 | 8/2014 | Tearney et al. |
| 2014/0275986 | A1* | 9/2014 | Vertikov ................ A61B 5/061 600/424 |
| 2014/0285878 | A1 | 9/2014 | Escuti et al. |
| 2015/0045622 | A1 | 2/2015 | Shishkov et al. |
| 2017/0035281 | A1 | 2/2017 | Takeuchi et al. |
| 2017/0176736 | A1 | 6/2017 | Yamamoto et al. |
| 2018/0017806 | A1 | 1/2018 | Wang et al. |
| 2018/0084981 | A1 | 3/2018 | Wang |
| 2018/0120212 | A1 | 5/2018 | Hosoda et al. |

FOREIGN PATENT DOCUMENTS

| | | |
|---|---|---|
| WO | 2007/084903 A2 | 7/2007 |
| WO | 2014031748 A1 | 2/2014 |
| WO | 2014104405 A1 | 7/2014 |
| WO | 2015116939 A1 | 8/2015 |
| WO | 2015116951 A2 | 8/2015 |
| WO | 2015116974 A1 | 8/2015 |
| WO | 2017/024145 A1 | 2/2017 |
| WO | 2017/106347 A1 | 6/2017 |
| WO | 2017/117203 A1 | 7/2017 |
| WO | 2017/139657 A1 | 8/2017 |
| WO | 2017/218496 A1 | 12/2017 |
| WO | 2018/013838 A1 | 1/2018 |
| WO | 2018/057924 A1 | 3/2018 |
| WO | 2018/132490 A1 | 7/2018 |

OTHER PUBLICATIONS

Pitris, C., et al., "A GRISM-based probe for spectrally encoded confocal microscopy", Optics Express, Jan. 27, 2003, pp. 120-124, vol. 11, No. 2.
Yelin, D., et al., "Three-dimensional miniature endoscopy", Nature, Oct. 19, 2006, pp. 765, vol. 443.
Kang, D., et al., "Miniature grating for spectrally-encoded endoscopy," Lab Chip, 2013, pp. 1810-1816, vol. 13.
Kang, D., et al., "Spectrally-encoded color imaging", Optics Express, Aug. 17, 2009, pp. 15239-15247, vol. 17, No. 17.
Yun, et al., "High-speed spectral-domain optical coherence tomography at 1.3 μm wavelength", Opt Express, Dec. 29, 2003, pp. 3598-3604, No. 11, vol. 26.
Tearney, G.J., et al., "Spectrally encoded miniature endoscopy", Optics Letters, Mar. 15, 2002, pp. 412-414, vol. 27, No. 6.
Bai, B., et al. "Optimization of nonbinary slanted surface-relief gratings as high-efficiency broadband couplers for light guides", Applied Optics, Oct. 1, 2010, pp. 5454-5464, vol. 49, No. 28.
Barlev, O., et al., "Design and experimental investigation of highly efficient resonance-domain diffraction gratings in the visible spectral region", Applied Optics, Dec. 1, 2012, pp. 8074-8080, vol. 51, No. 34.

* cited by examiner

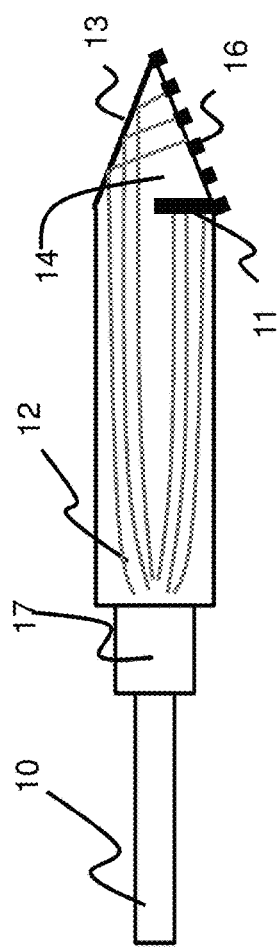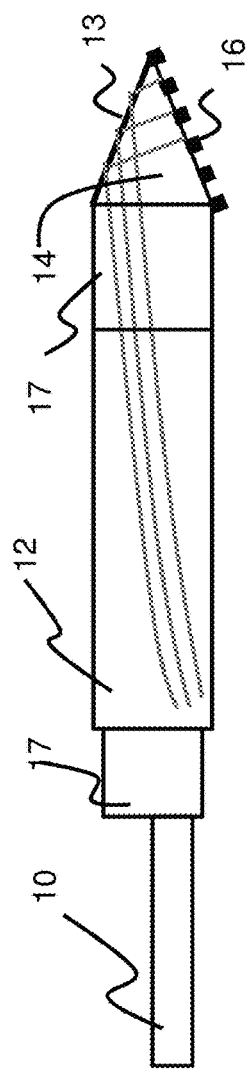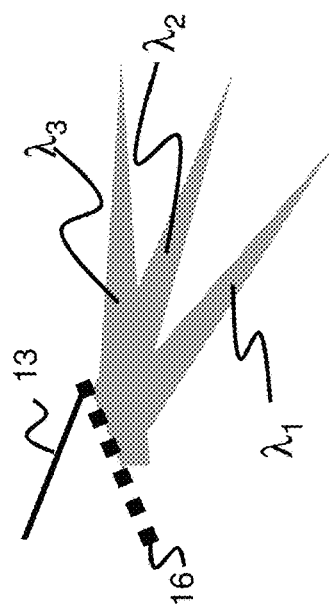

OPTICAL PROBE, LIGHT INTENSITY DETECTION, IMAGING METHOD AND SYSTEM

CROSS-REFERENCE TO RELATED APPLICATION(S)

This application is a national stage application of PCT/US15/13816 filed 30 Jan. 2015 and claims priority to U.S. Provisional Application Ser. No. 61/934,486 filed Jan. 31, 2014, the content of each of which are incorporated herein by reference in their entirety.

This application relates to U.S. Provisional Application Ser. No. 61/934,421 (System and method for fabrication of miniature endoscope using nanoimprint lithography), filed Jan. 31, 2014, and to U.S. Provisional Application Ser. No. 61/934,464 (Apparatus and methods for color endoscopy), filed Jan. 31, 2014, the entire contents of such disclosures are incorporated herein by reference.

FIELD OF THE DISCLOSURE

The present disclosure relates generally to exemplary apparatus and method for endoscopy and, more particularly to exemplary spectrally encoded endoscopy probes for obtaining information of forward direction, exemplary methods for acquiring the image, and exemplary methods of making the endoscope.

BACKGROUND INFORMATION

Medical probes have the ability to provide images from inside the patient's body. Considering the potential damage to a human body caused by the insertion of a foreign object, it is preferable for the probe to be as small as possible. Additionally, the ability to image within small pathways such as small vessels, small ducts, small needles, cracks etc., requires a small probe size.

One useful medical probe employs a spectrally encoded endoscopy ("SEE"), which is a miniature endoscopy technology that can conduct high-definition imaging through a sub-mm diameter probe. With SEE, broadband light is diffracted by a grating at the tip of the fiber, producing a dispersed spectrum on the sample. Light returned from the sample is detected using a spectrometer; and each resolvable wavelength corresponds to reflectance from a different point on the sample. The principle of the SEE technique and an SEE probe with a diameter of 0.5 mm, i.e., 500 µm have been described in D. Yelin et al., Nature Vol. 443, 765-765 (2006). SEE can produce high-quality images in two- and three-dimensions.

One of the technical challenges for fabricating SEE probes has been to conduct forward-view SEE imaging (also called front-view SEE imaging). Previously, SEE probe designs that utilize double-prism grating prism (DP GRISM) have been proposed for forward-view imaging by publication U.S. 2011/0237892. While a previous publication (Optics Express, 11(2):120-4, 2003) demonstrated a spectrally-encoded confocal microscopy (SECM) probe that uses a DP-GRISM. However, the diameter of the probe was 10 mm, and there are numerous challenges in miniaturizing the DP GRISM to a size that is useable in SEE probe.

Accordingly, it can be beneficial to address and/or overcome at least some of the deficiencies indicated herein above, and thus to provide a new SEE probe that can view forward direction and an apparatus to use such a probe, e.g., for imaging in a small optics.

SUMMARY OF EXEMPLARY EMBODIMENTS

Thus, to that end, apparatus, systems, and methods for miniature endoscopes that conduct forward-view imaging according to an exemplary embodiment of the present disclosure can be provided. According to such exemplary embodiment, apparatus, methods and system can be provided for fabricating SEE probes that conduct forward-view imaging.

According to certain exemplary embodiments of the present disclosure, a probe comprising, from proximal end to distal end, a light guiding component, a light focusing component, a light reflecting component, and a grating component can be provided. The probe optical axis can be defined as the direction of propagation of a light from the light guiding component through the light focusing component. For this exemplary probe, the light reflecting component and the grating component can be positioned such that, when a light is transmitted to the grating component, at least one diffracted light can be propagated from the grating component substantially along the probe optical axis. In some exemplary embodiments, the diffracted light(s) can propagate from the grating component at less than 1° from the probe optical axis.

In some exemplary embodiment of the present disclosure, the light reflecting component can be or include a part of a spacer that has an angled reflective side surface. The angled reflective side surface makes the incidence angle on the grating in such a way that at least one of the wavelengths propagates parallel to the optical axis of the lens. The SEE probe can be rotated 360° to acquire two-dimensional images of the tissue from the forward view.

According to another exemplary embodiment, an additional fiber can be used alongside with the SEE illumination optics. In this exemplary embodiment, reflected light from the tissue can be collected by the additional fiber, which can significantly reduce the background signal from the probe.

In yet other exemplary embodiments of the present disclosure, the SEE probe can be configured to have two spectrally-encoded illuminations on the tissue, one on the opposite side from the other relative to the rotation axis of the SEE probe. This exemplary embodiment makes it possible to image the tissue with two or more wavelengths, which can provide color images of the tissue.

In yet other exemplary embodiments of the present disclosure, a method of color imaging can be provided, where the SEE probe can be rotated around the probe optical axis, and at least two images can be obtained per rotation. Such two or more images can then be combined into a single color image.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIG. 4A is a diagram of a front-view SEE probe according to an exemplary embodiment of present disclosure;

FIG. 4B is a diagram of the front-view SEE probe according to another exemplary embodiment of present disclosure; and FIG. 4C is an exemplary illustration of how the light is diffracted with the front-view SEE probe of the exemplary embodiments of present disclosure shown in FIGS. 4A and/or 4B.

Figure 1:
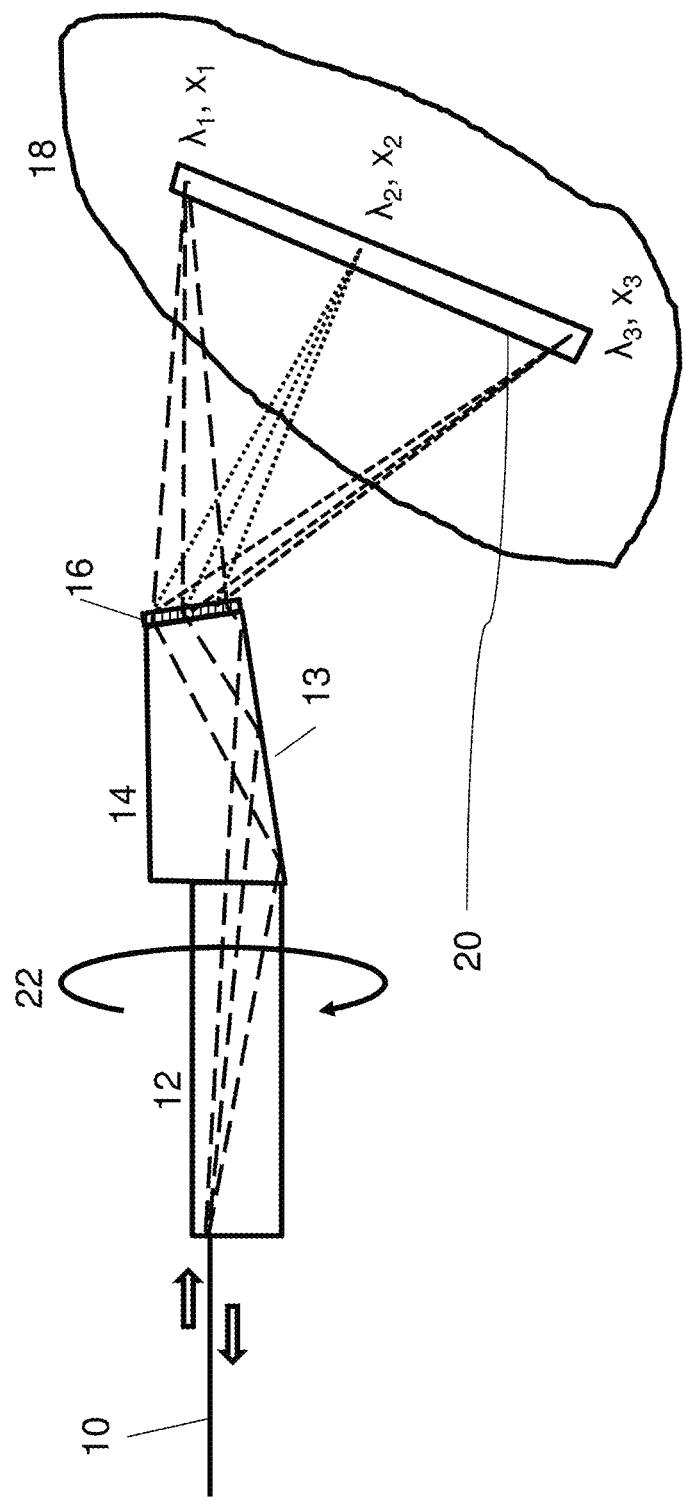
FIG. 1 is a diagram of an exemplary SEE probe according to an exemplary embodiment of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

A diagram of an exemplary embodiment of the SEE probe according to the present disclosure is shown in FIG. 1. This exemplary SEE probe can include an optical fiber 10, a focusing lens 12, and a spacer 14, and a diffraction grating 16. Broadband light (or other electro-magnetic radiation) can be coupled or otherwise provided into the fiber 10, and focused by the lens 12. One side of the spacer 14 can be angle-polished, and can operate as a reflective surface so as to provide a light reflecting component 13. The light (or other electro-magnetic radiation) after the lens 12 can be reflected by this angle-polished surface of the light reflecting component 13, and can become incident on the grating 16. The angle-polished surface can have, for example, a metallic or dielectric coating to increase the reflectivity thereof. The light (or other electro-magnetic radiation) can then be diffracted by the grating component 16, and each wavelength λ can be focused on a unique spatial location on the tissue 18, as shown in FIG. 1 as $X_1$, $X_2$, and $X_3$ for wavelengths $\lambda_1$, $\lambda_2$, and $\lambda_3$. Therefore, the light (or other electro-magnetic radiation) can be focused into a line 20 (shown as spectrally-encoded line in FIG. 1), rather than onto a point. One of the wavelengths in the light can propagate parallel to the optical axis of the lens, shown as $\lambda_1$ shown in FIG. 1. The location and angle of the fiber 10 relative to the lens 12 can be adjusted so that at least one of the wavelengths of the illumination light is co-linear to the lens optical axis after the grating 16. Light (or other electro-magnetic radiation) reflected by the tissue 18 can be coupled or otherwise provided back to the fiber 10, and then can be delivered to a spectrometer (not shown). At the spectrometer, the spectrum of the returning light (or other electro-magnetic radiation) can be read out, which can be used to generate a line image of the tissue using a computer (not shown). The exemplary SEE probe can be scanned rotationally along the optical axis of the lens as shown by the arrow 22, e.g., by rotating the lens 12 and/or the spacer 14, or in other ways which should be understood to those having ordinary skill in the art.

Figure 2:
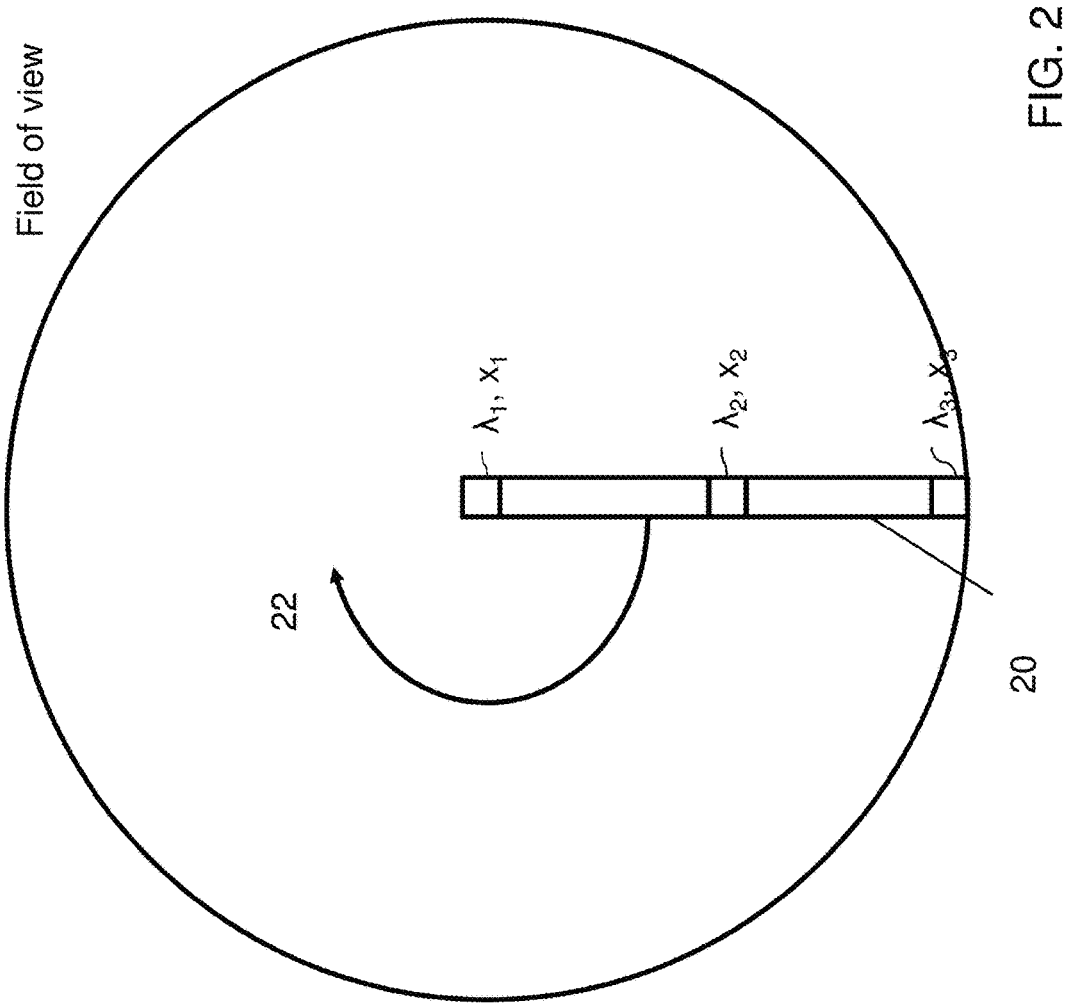
FIG. 2 is an exemplary illustration of the field of view that can be obtained by the probe shown in FIG. 1.

FIG. 2 shows a field of view that can be obtained by the exemplary SEE probe shown in FIG. 1. For example, by rotating the spectrally encoded line 20 with the rotational axis at one end of the spectrally-encoded line, a circular region can be imaged. This circular region can be located approximately perpendicular to the SEE probe, and therefore, the exemplary SEE probe shown in FIG. 1 can conduct forward-view imaging.

Figure 3:
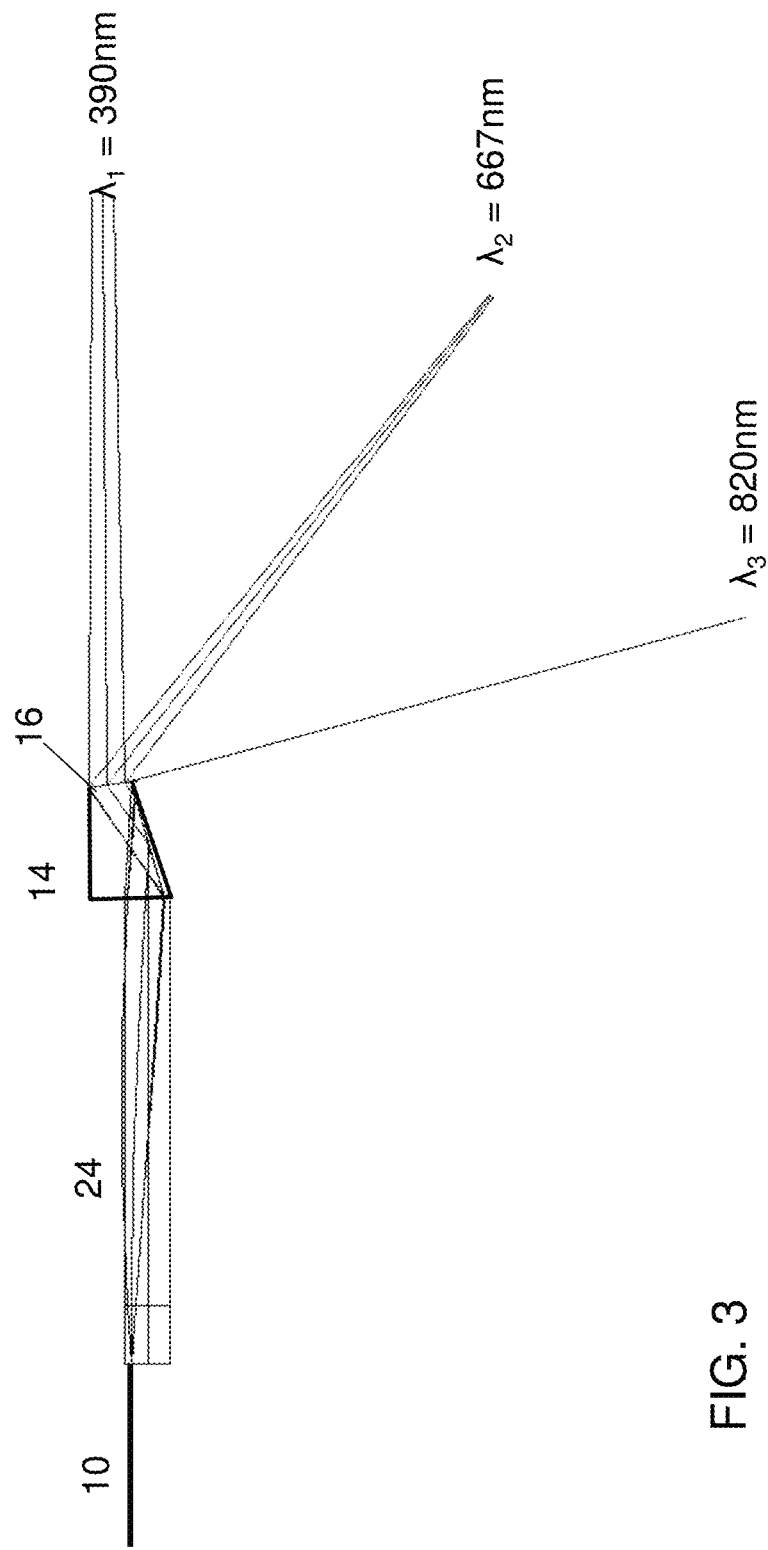
FIG. 3 is a diagram showing an exemplary irradiation generated in an optical simulation software, ZEMAX, according one exemplary embodiment of the present disclosure.

FIG. 3 shows an illustration of radiations generated using an optical simulation software, ZEMAX, according one exemplary embodiment of the present disclosure generated. To generate such illustration, e.g., a gradient index (GRIN) lens 34 (SRL, GoFoton; length=3.48 mm; diameter=0.35 mm) can be used as the focusing lens, according to another exemplary embodiment of the present disclosure. The diffraction grating 16 with a groove density of 2000 lines/mm can also used. In this exemplary configuration, the spectral band of 390-820 nm can produce a field angle of 75°. The propagation angle of the 390 nm light can be parallel to the optical axis of the GRIN lens 34.

An exemplary front-view SEE probe according to certain exemplary embodiments of the present disclosure can have a light reflection component in the probe, as shown in FIGS.

4A and 4B. For example, as shown in FIG. 4A, the light (or other electro-magnetic radiation) can be guided by the optical fiber 10, which can be or include, for example, a single-mode fiber, a-few-mode fiber, or a multi-mode fiber. The outer diameter of a fiber cladding of the fiber 10 can be typically 125 μm, and may be modified if desired. The light is a mixture of various wavelengths that is generally in the visible spectrum, and may also extend into the UV or near IR, as well as into other ranges. The exemplary range of the wavelength can be typically from 400 nm to 800 nm. The light (or other electro-magnetic radiation) can be slightly focused after passing though the light focusing component. When the light passes through the light focusing component, it can propagate in a transparent media against the input wavelength.

The fiber 10 can be directly spliced to the light focusing component 12 and/or an optional transparent insert 17 may be inserted between the optical fiber 12 and the light focusing component 12. The insert 17 can be or include a glass rod or a so-called coreless fiber. For miniaturization, a gradient index (GRIN) lens can be optionally used for the light focusing component 12 because the diameter of the GRIN lens can be as small as, for example, 350 μm. A transparent media can be located between the light focusing component 12 and the grating 16, and can act as the spacer 14. This spacer 14 can be, for example, air, glass, or epoxy. In some exemplary embodiments, an angle-cut GRIN lens can be used as a combination of the light focusing component 12 and the spacer 14.

According to certain exemplary embodiments of the present disclosure, the insert 17 and the spacer 14 can be provided in a single component and/or may be integrally combined. One end of the spacer 14 can be angled and provided with the reflective surface 13, such as, e.g., by including a metallic or dielectric coating. The grating 16 can have various forms, such as, e.g., standard groove grating, blazed grating, or volume grating including holographic grating and so on. The light (or other electro-magnetic radiation) can be diffracted by the grating 16 to reach the object (e.g., the tissue). Another optical fiber can be bundled to and/or in the exemplary SEE probe of FIG. 4A or 4B for detecting the scattered light from the object.

FIG. 4A shows a diagram of the exemplary probe according to another exemplary embodiment of the present disclosure that also has the light reflection component 13 and a light blocking component 11. The light blocking component 11 can block nearly half bottom of the light focusing component 12. The light reflection component 13 can be or include, for example, a mirror. If the spacer 14 has enough high refractive index (e.g., greater than 1.35), a polished surface of the light reflection component 13 can act as a mirror due to the nature of a total internal reflection. To clarify the operation, a schematic ray tracing result after the insert 17 is also illustrated in FIG. 4A. For example, a ray bundle above the light blocking component 11 can impact the light reflection component 14 which can be reflected and illuminates the grating 16. The grating 16 deflects the light to forward direction, i.e., along the reference axis. The reference axis as described herein can be defined as (but not limited to) the axis along which a light beam does not bend at the first surface of the light focusing component 12.

Thus, the exemplary probe described in this exemplary embodiment can be configured such that light reflecting from the light reflecting component undergoes total internal reflection. Total internal reflection occurs in the case of an internal reflection. It can be assumed that light propagates from a media with a refractive index $n_i$ to a media with a refractive index $n_t$, where $n_i > n_t$. An angle $\theta_c$ can be defined as $\sin \theta_c = n_t/n_i$. If the incident angle is greater or equal to the angle $\theta_c$, the incident light can be fully reflected and thus the boundary can behave like mirror.

Another exemplary configuration of the probe according to another exemplary embodiment is shown in FIG. 4B. In the exemplary configuration of FIG. 4B, the fiber 10 can be off-set downward from the center of the light focusing component 12. With this exemplary configuration, the light is directed upward and impacts the light reflection component 13. The optional insert 17 may be inserted between the light focusing component 12 and the spacer 14 to effectuate all the light to impact the mirror 13. According to this exemplary embodiment, the light blocking component 11 can be optionally added to the exemplary embodiment shown if FIG. 5B.

One of the exemplary features of such exemplary probe is that the longer wavelength can be deflected closer to the direction of reference axis. For example, three wavelengths $\lambda_1$, $\lambda_2$, and $\lambda_3$ ($\lambda_3 > \lambda_2 > \lambda_1$) can be guided into the exemplary probe shown in FIG. 4A. After the grating 16, the diffracted light can have the appearance as shown in FIG. 4C.

According to further exemplary embodiments of the present disclosure, the light focusing component 12 can be or include a GRIN lens. With the exemplary GRIN lens, rays approximately follow sinusoidal paths. A pitch of GRIN lens can be determined such that a light ray that has propagated one pitch has propagated one cycle of the sinusoidal path trajectory. Therefore, the GRIN lenses with lengths of one pitch and two-pitch have the identical optical property. For example, let $G_p$ be one pitch of a GRIN lens. In some embodiments, the front-view SEE probe with the GRIN lens has a GRIN lens with a length that is more than $(0.5 \ k+0.25)G_p+0.1G_p$ and less than $(0.5 \ k+0.25)G_p+0.3G_p$, where k is zero or a positive integer. In some exemplary embodiments, the length of the GRIN lens can be more than $0.35G_p$ and less than $0.55G_p$. This exemplary result facilitates a determination of the configuration for the front-view SEE probe design and assists in simplifying the manufacture thereof.

Alternatively, other focusing component(s), such as micro lens(es), can be used instead of a GRIN lens.

Figure 5:
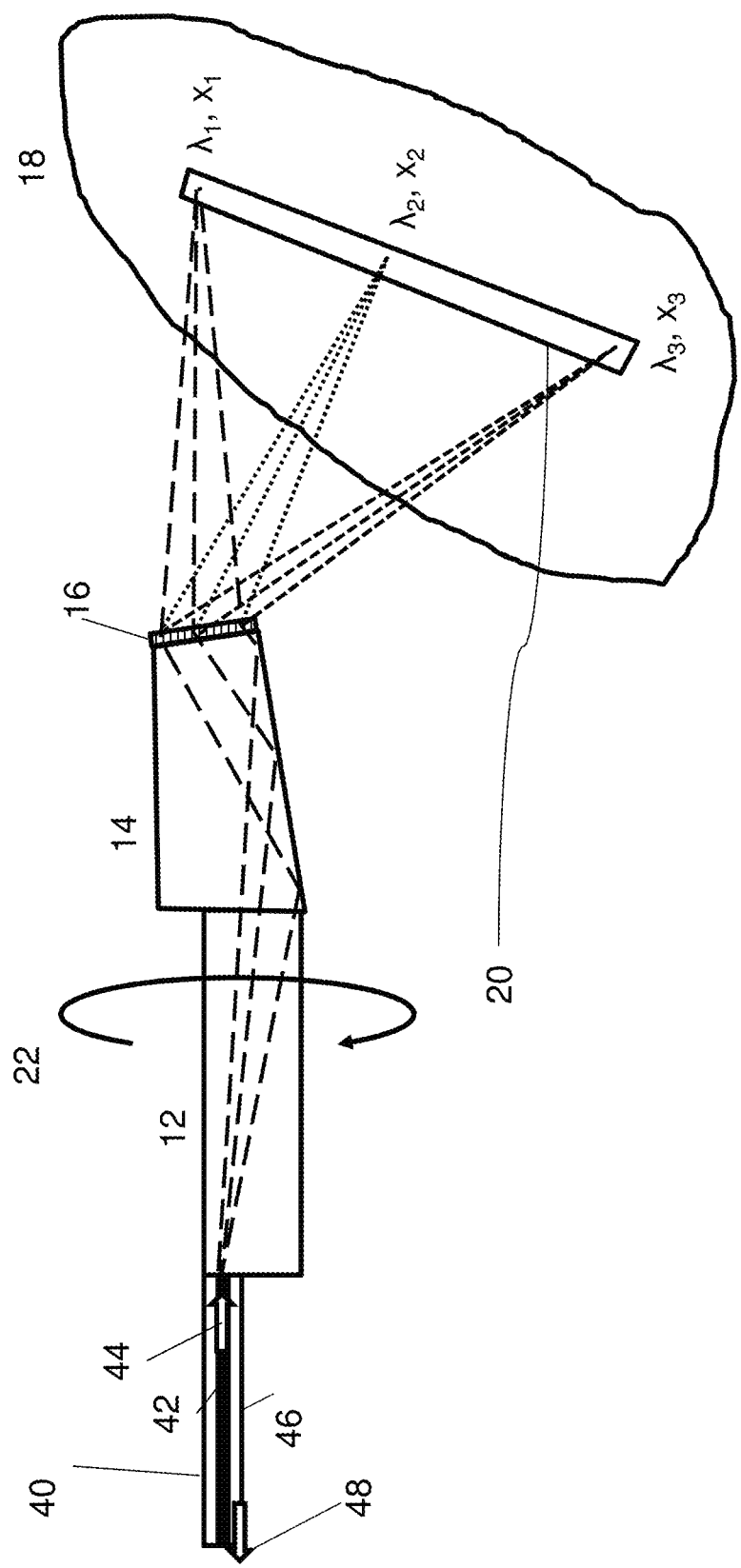
FIG. 5 is a diagram of the exemplary SEE probe according to a further exemplary embodiment of the present disclosure that uses a double-clad fiber for illumination and detection.

FIG. 5 shows a diagram of the probe according to yet another exemplary embodiment of the present disclosure. In this exemplary embodiment, the optical fiber can be or include a double-clad fiber (DCF) 40. A core of the DCF 42 can be used for an illumination 44, and an inner cladding of the DCF 46 can be used for a detection 48. This exemplary probe can be used to reduce the speckle noise by using the large-diameter inner clad 46 as the detection aperture.

Figure 6:
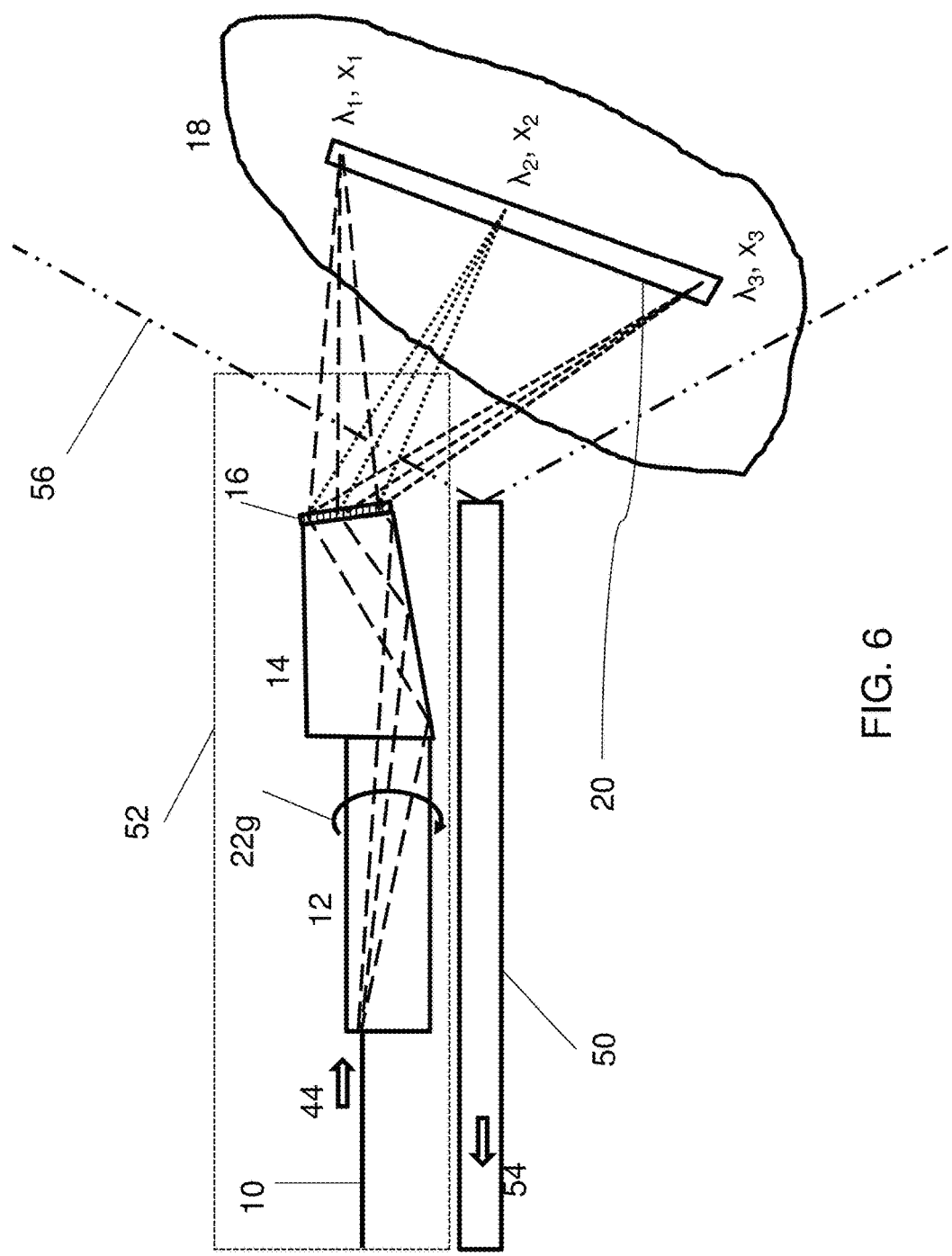
FIG. 6 is a diagram of the exemplary SEE probe according to still another exemplary embodiment of the present disclosure that uses an additional fiber for detection.

FIG. 6 shows a diagram of the probe according to still another exemplary embodiment of the present disclosure. In this exemplary embodiment, an additional optical fiber (e.g., a detection fiber) 50 can be used to collect light reflected from the tissue. With such exemplary probe, it is possible to provide a rejection of background signal generated from the probe itself by having two separate optical paths for the illumination and/or the detection. Illumination optics 52, e.g., which can be composed of the illumination fiber 10, lens 12, spacer 14, and grating 16, can be rotated, while the detection fiber 50 can be stationary. An acceptance angle of the detection fiber 56 can be same or larger than the field angle made by the spectrally-encoded line 20. The detection fiber 50 can be a high-NA multi-mode fiber, which can have a relatively large wave-guiding area for effective light collection. The detection fiber 50 can have a refractive element at the distal tip to increase the acceptance angle on the sample space if, e.g., the NA of the fiber itself is not high enough.

Figure 7B:
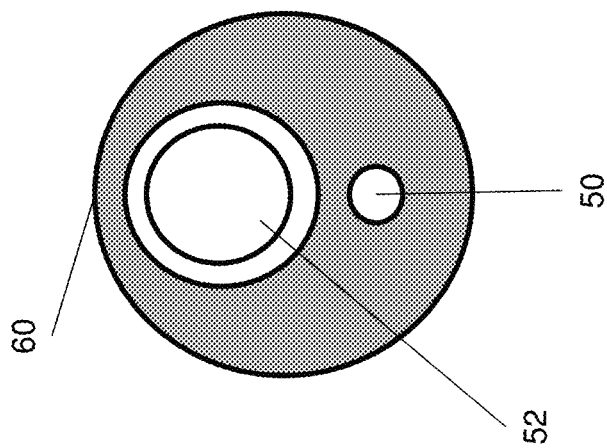
FIG. 7B is a front view of the exemplary guiding tube or the needle shown in FIG. 7A.
Figure 7A:
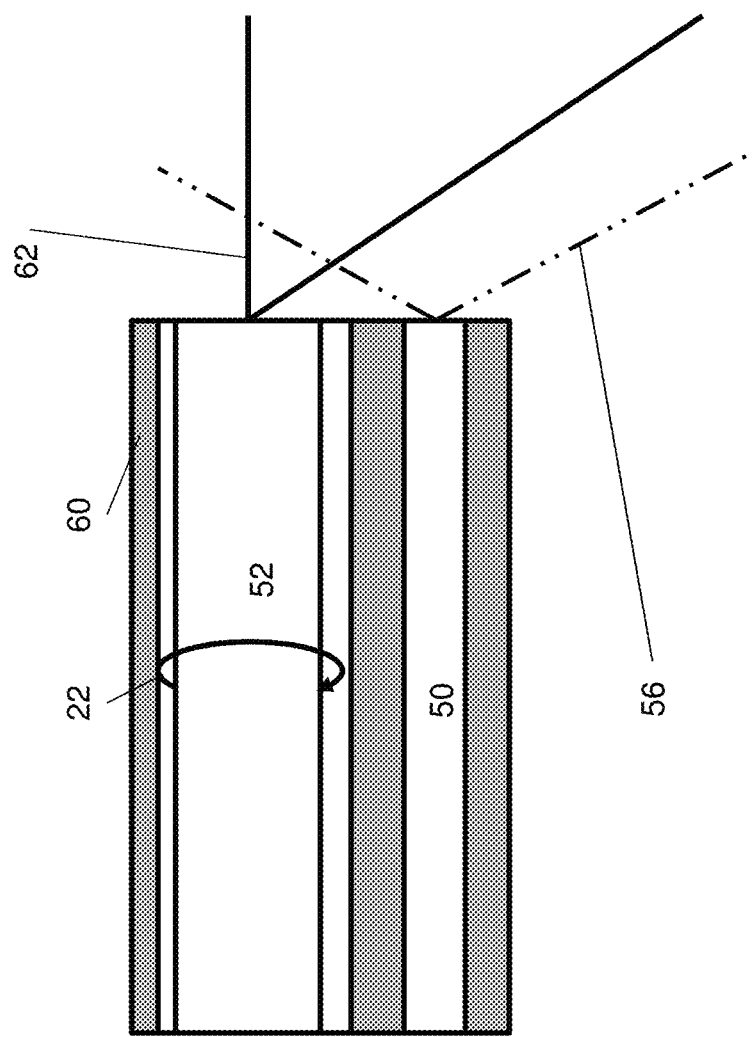
FIG. 7A is a side view of an exemplary guiding tube and/or a needle according to an exemplary embodiment of the present disclosure.

FIGS. 7A and 7B side and front views of an exemplary guiding tube and/or a needle according to another exemplary embodiment of the present disclosure. In this exemplary embodiment, the guiding tube or the needle 60 can be used to encase the illumination optics 52 and the detection fiber 50. The guiding tube or the needle 60 can have multiple lumens, and/or one of the lumens can be used to house the illumination optics 52. Another lumen can be used to house the detection fiber 50. Inside the guiding tube or the needle 60, the illumination optics 52 can be rotationally scanned to provide two-dimensional images where the filed angle of the illumination optics 62 is, for example, doubled due to the rotation. The guiding tube or the needle 60 can be made, for example, of or include metallic tubings and/or semi-flexible polymer tubings.

Figure 8:
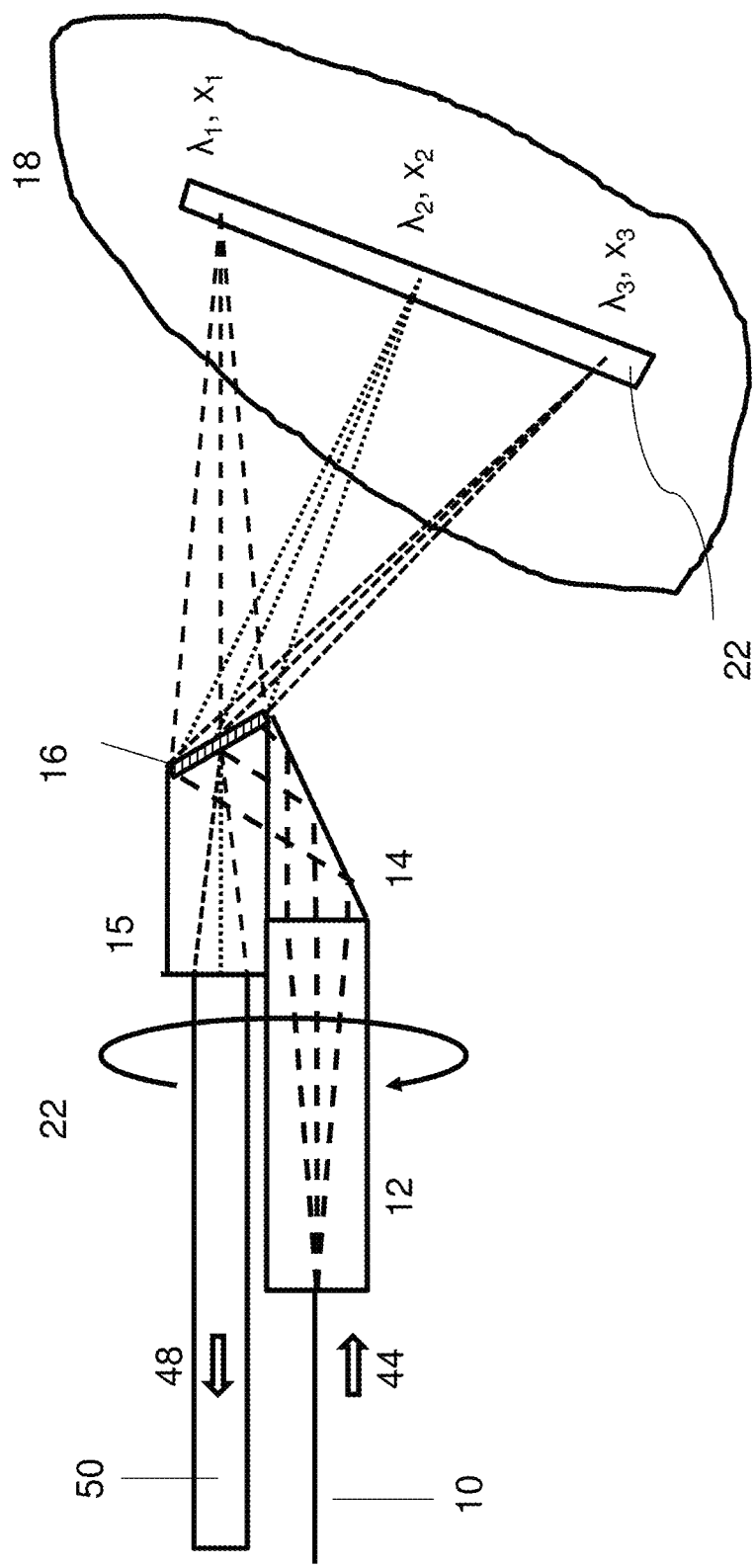
FIG. 8 is a diagram of the exemplary SEE probe according to yet a further exemplary embodiment of the present disclosure that uses different diffraction orders for illumination and detection.

FIG. 8 shows a diagram of the probe according to yet another exemplary embodiment of the present disclosure. In this exemplary embodiment, the detection fiber 50 can be placed behind the grating 16. The detection fiber 50 can be or include, for example, a high-NA multi-mode fiber, which has a relatively large wave-guiding area for effective light collection. The probe can have 2 (or more) spacers, e.g., the spacer (the spacer 14) next to the lens 12, and another spacer (spacer 15) between the grating 16 and the detection fiber 50. The illumination light 44 from the lens 12 can be reflected by the surface of the spacer 14, go into the spacer 15, and can be diffracted by the grating 16 on the spacer 15 to the first diffraction order direction toward the tissue 18. The reflected light from the tissue 18 can be diffracted by the grating 16 to the 0th diffraction order direction, and collected by the detection fiber 50 through the spacer 15. The optics, e.g., composed of the illumination fiber 10, lens 12, spacer 14, spacer 15, grating 16, and detection fiber 50 can be rotated together, as shown by the rotational direction 22 in FIG. 8. According to this exemplary embodiment, the probe diameter can be provided smaller than that of the exemplary embodiment in which the detection fiber is placed outside of the illumination optics.

In some exemplary embodiments, the GRIN lens and/or other focusing component can be cut in half or otherwise truncated along the optical axis instead of or in addition to inserting the light blocking component. For example, the light focusing component can be cut, ground, or divided in about half.

Figure 9A:
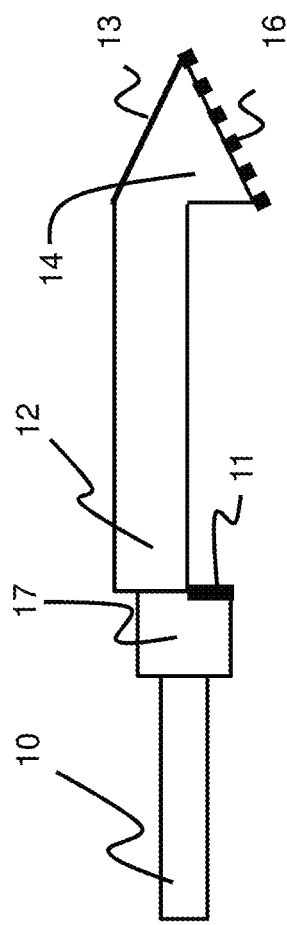
FIGS. 9A-9C are diagrams of exemplary variations of the front-view SEE probe according to the present disclosure.
Figure 9B:
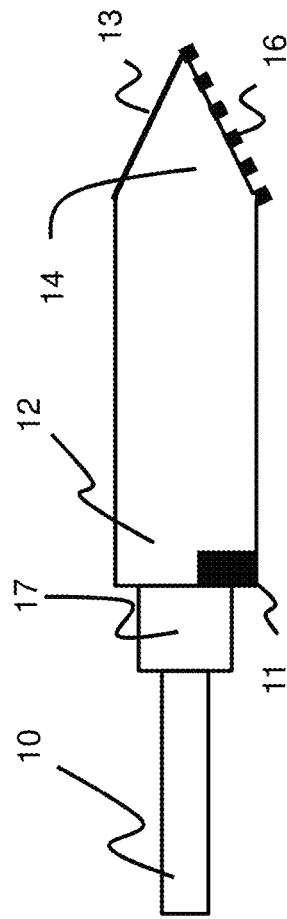
Figure 9C:
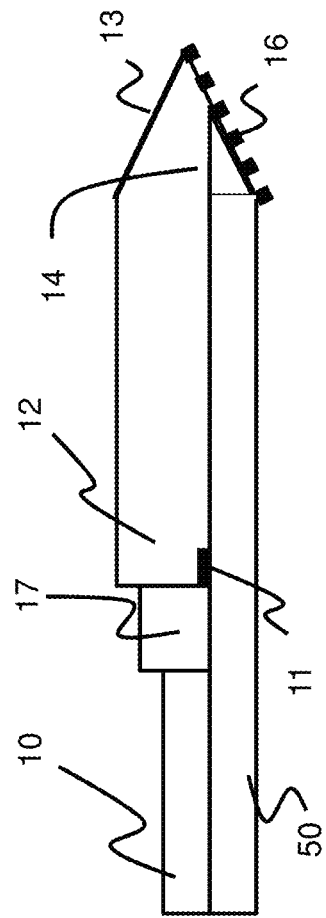

One advantage of using a truncated light focusing component can be that such exemplary configuration can provide an additional space in the probe. For example, if a 350 µm diameter GRIN lens is used where the bottom half of the lens is removed, additional space with a maximum height of 175 µm can be gained (see FIG. 9A). This additional space can be used for, for example, a placement of the detection fiber, and thus can assist in the miniaturization of the exemplary front-view SEE probe. Example of various front-view SEE probes according certain exemplary embodiment of the present disclosure are shown in FIGS. 9A-9C. If the extra space is not needed, a portion of the GRIN lens can be blocked as shown in FIG. 9B. In FIG. 9C, the detection fiber 50 can be bundled at the bottom of the GRIN lens whose bottom is cut-off, thus potentially allowing a smaller diameter probe to be formed.

Figure 10B:
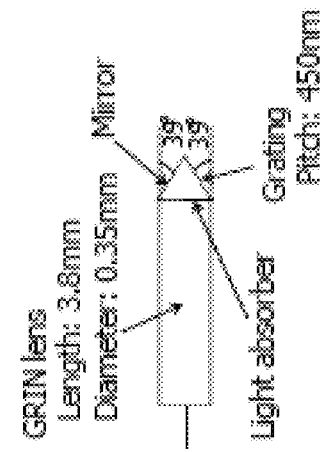
FIGS. 10A-10C are diagrams of exemplary variations of the front-view SEE probe of according to the present disclosure.
Figure 10C:
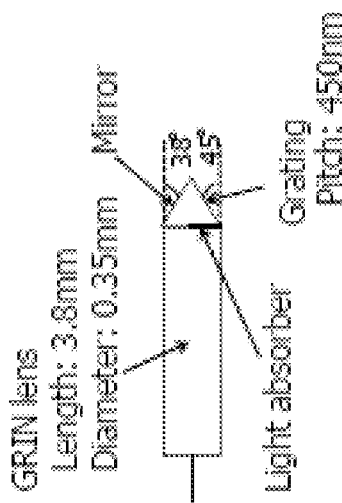
Figure 10A:
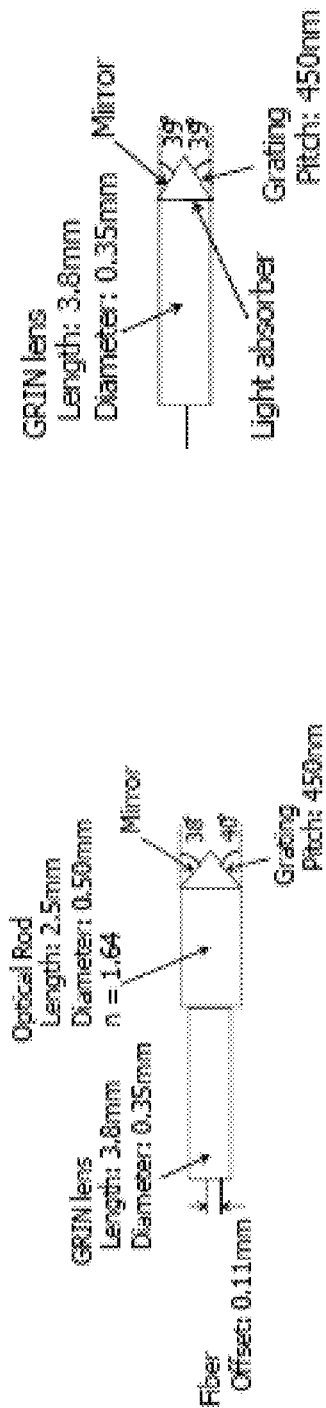

Two angles (e.g., positioning of the light focusing component and the spectrally dispersive component) from the optical axis may generally be slightly different. This is shown in FIGS. 10A-10C. In FIG. 10A, for example, the mirror is at 38° while the grating is at 40°. Thus, it may be beneficial, for division of the focusing element, to either add a light absorber or cut the focusing element in half, thereby being slightly less than 50%.

Figure 11:
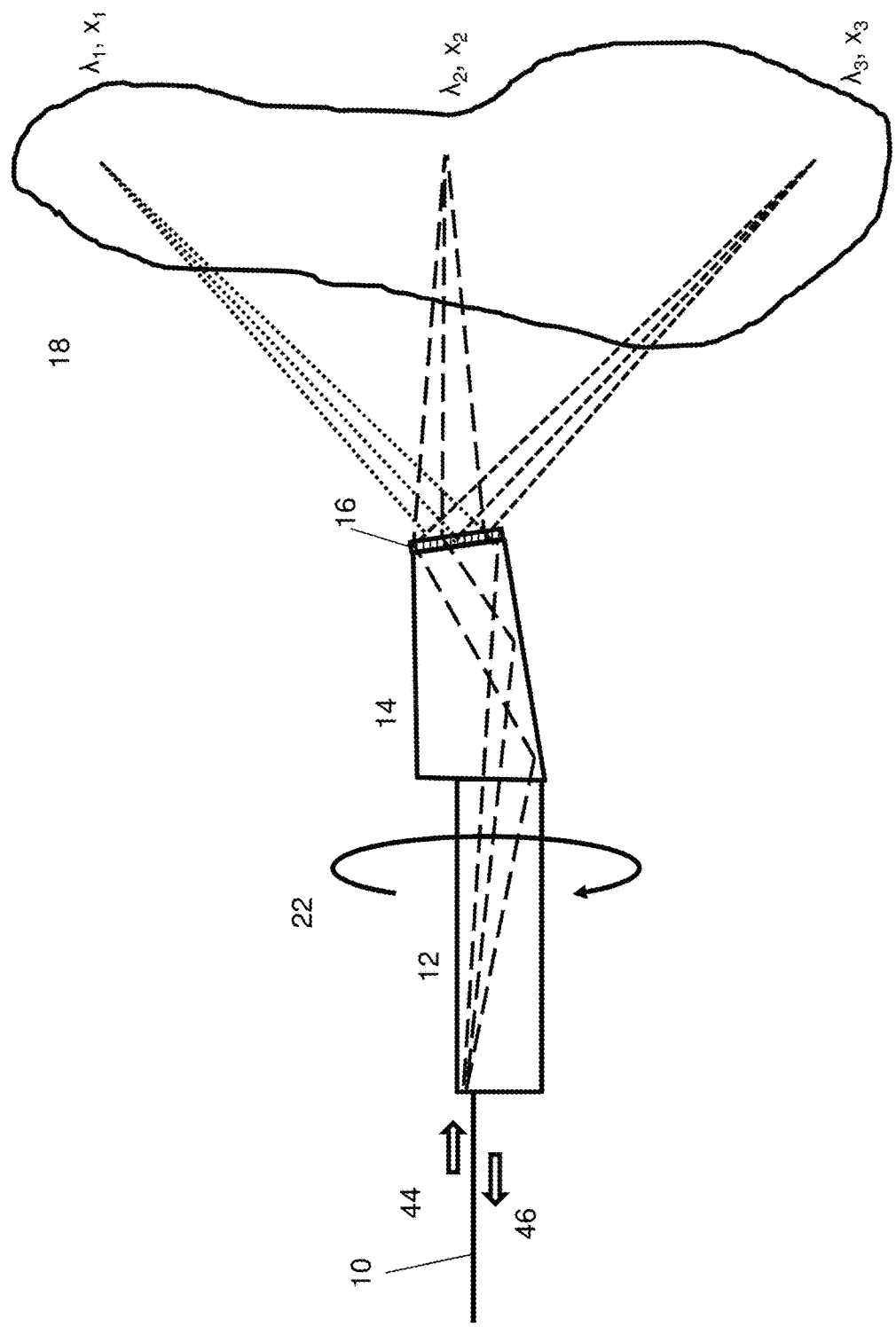
FIG. 11 is a diagram of the exemplary SEE probe according to another exemplary embodiment of the present disclosure that can conduct dual-color imaging.

FIG. 11 shows a diagram of the probe according to yet another exemplary embodiment of the present disclosure. In this exemplary embodiment, the spectrally-encoded line spreads above and below the center of the field of view. Wavelength approximately at the center of the working spectrum can be configured to propagate parallel to the optical axis of the lens. An upper half of the tissue 18 can be illuminated by a shorter half of the working spectrum, and a lower half of the tissue 18 can be illuminated by a longer half of the working spectrum. By rotating the exemplary SEE probe, the entire field of view can be imaged by both the shorter and longer halves of the working spectrum. For example, the grating 16 can have the groove density of 2500 lines/mm, the shorter half of the spectrum can be 448 to 560 nm, and the longer half can be 560 to 800 nm. With these exemplary parameters, the exemplary SEE probe can image ±21° field angle, and the tissue 18 can be sampled by two wavelengths, each of which can approximately represent one of the red and green colors. This dual-color imaging capability can be useful in visualizing vasculature in the tissue 18. In other exemplary embodiments, a different separation of the spectrum into two parts can be effectuated at a different point on the spectrum.

Figure 12:
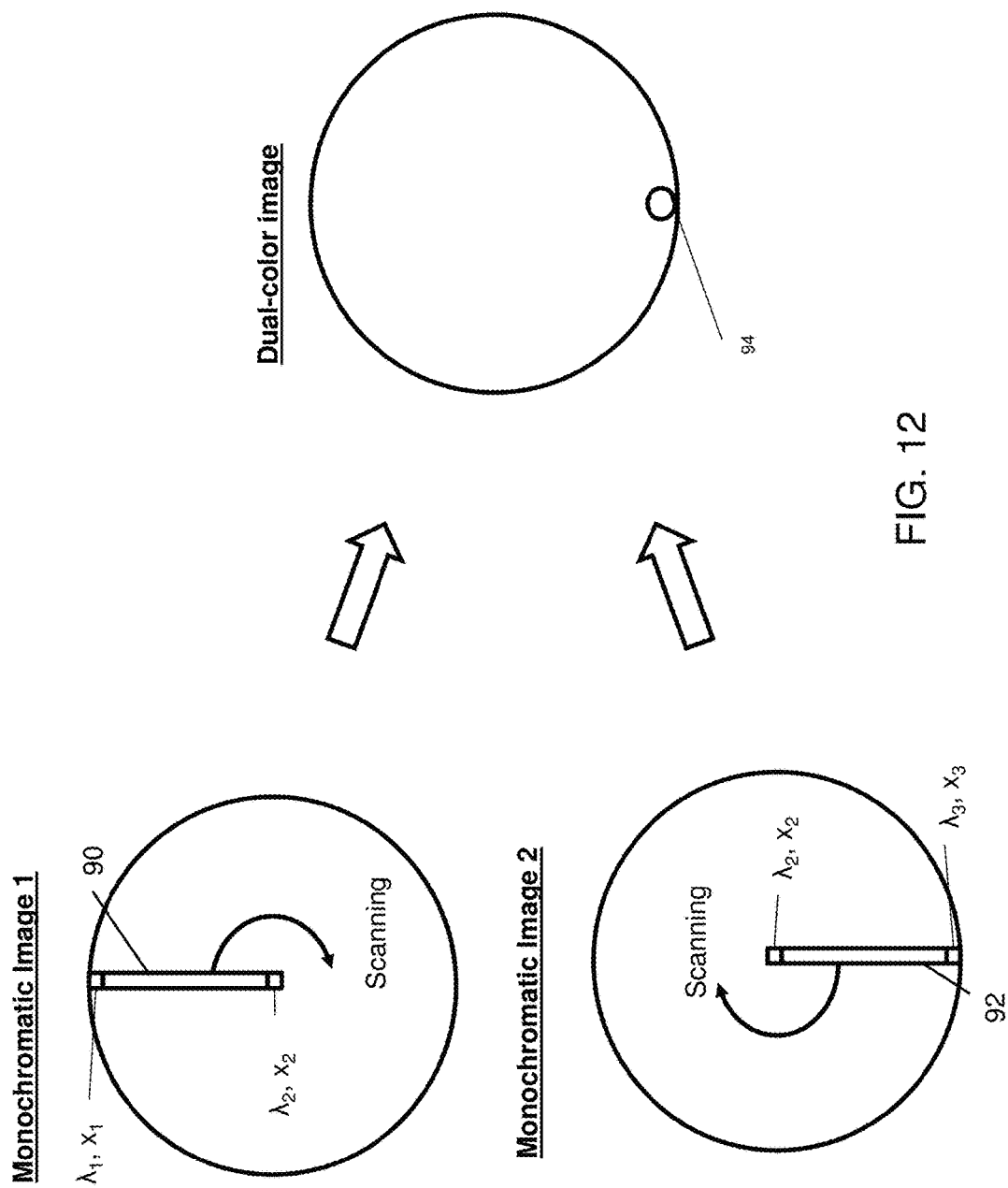
FIG. 12 is a set of illustrations of the dual-color images that can be obtained by the SEE probe according to various exemplary embodiments of the present disclosure.

FIG. 12 shows a set of illustrations of the dual-color images that can be obtained by the SEE probe according to various exemplary embodiments of the present disclosure. For example, a monochromatic image can be obtained by scanning the first spectrally-encoded line 90, which can correspond to the shorter half of the working spectrum. Another monochromatic image can be obtained by scanning the second spectrally-encoded line 92, which can correspond to the longer half of the working spectrum. The exemplary (e.g., two) monochromatic images can be combined to generate a dual-color image as shown on the right side of FIG. 12, where each point has been imaged by two wavelengths of light, as exemplified by point 94, which was imaged by light at wavelengths $\lambda_1$ and $\lambda_3$.

Figure 13:
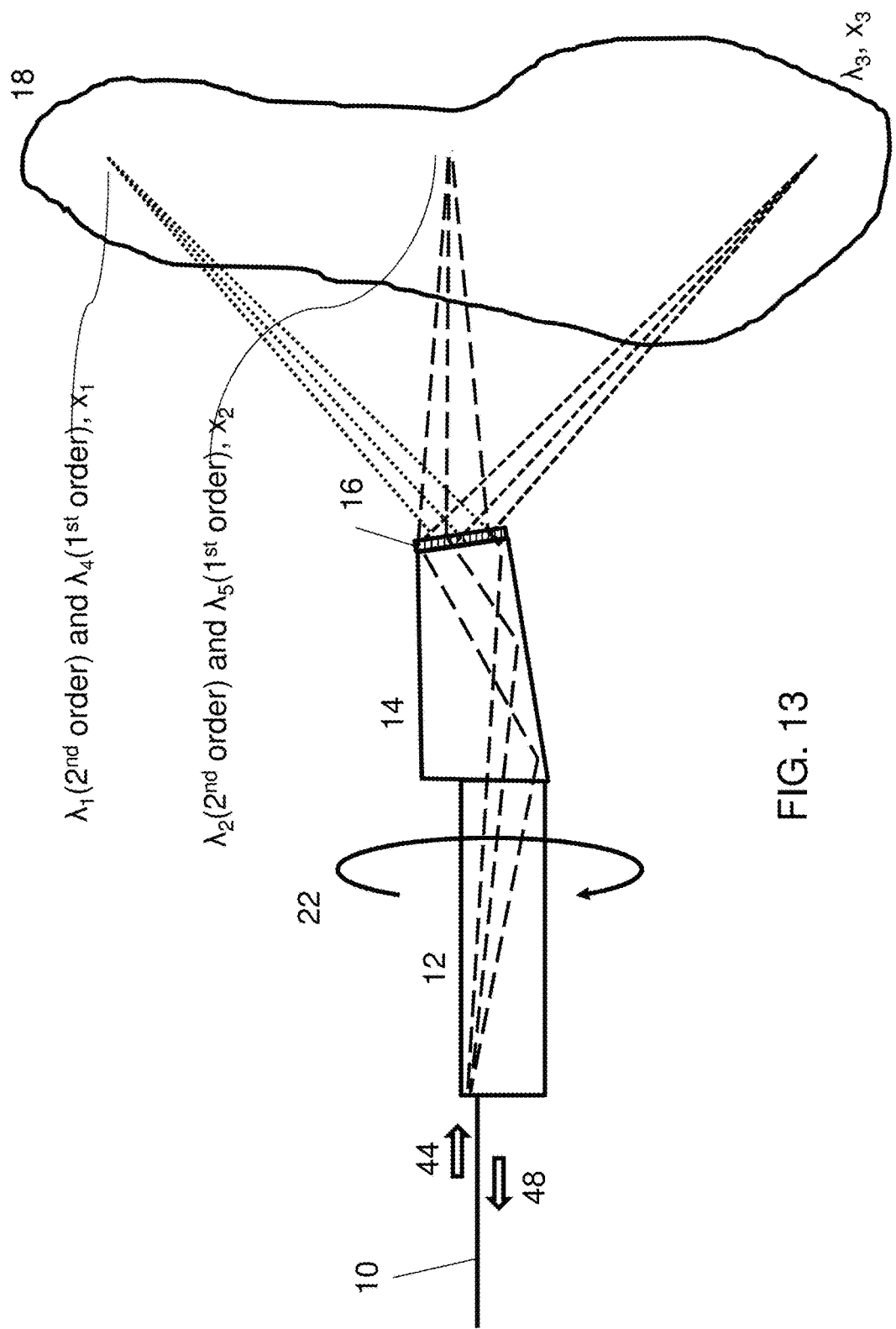
FIG. 13 is a diagram of the exemplary SEE probe according to a further exemplary embodiment of the present disclosure that can conduct tri-color imaging.

FIG. 13 shows a diagram of the probe according to a further exemplary embodiment of the present disclosure. In this exemplary embodiment, the grating 16 can direct light with two wavelengths to the same direction by using different diffraction orders. The light with the short wavelength $\lambda_1$ can be directed to the point $x_1$ by the $2^{nd}$ order diffraction. The light with the longer wavelength $\lambda_4$ can be directed to the same point $x_1$ by the $1^{st}$ order diffraction. With this exemplary configuration, each point of the tissue 18 can be imaged by at least three different wavelengths.

For example, the grating 16 can have the groove density of 1250 lines/mm, the first spectrum can be 439-500 nm; the second 500-575 nm; and the third 878-1000 nm. With these parameters, the exemplary SEE probe can image a field angle of ±14°, and each point of the tissue 18 is imaged by three wavelengths, each of which can approximately represent the blue, green and NIR spectra. Since the absorption coefficient of the tissue 18 can be significantly smaller in both red and NIR regions than those in blue and green regions, the image taken by the NIR spectrum can be used to represent the red channel of the image.

Figure 14:
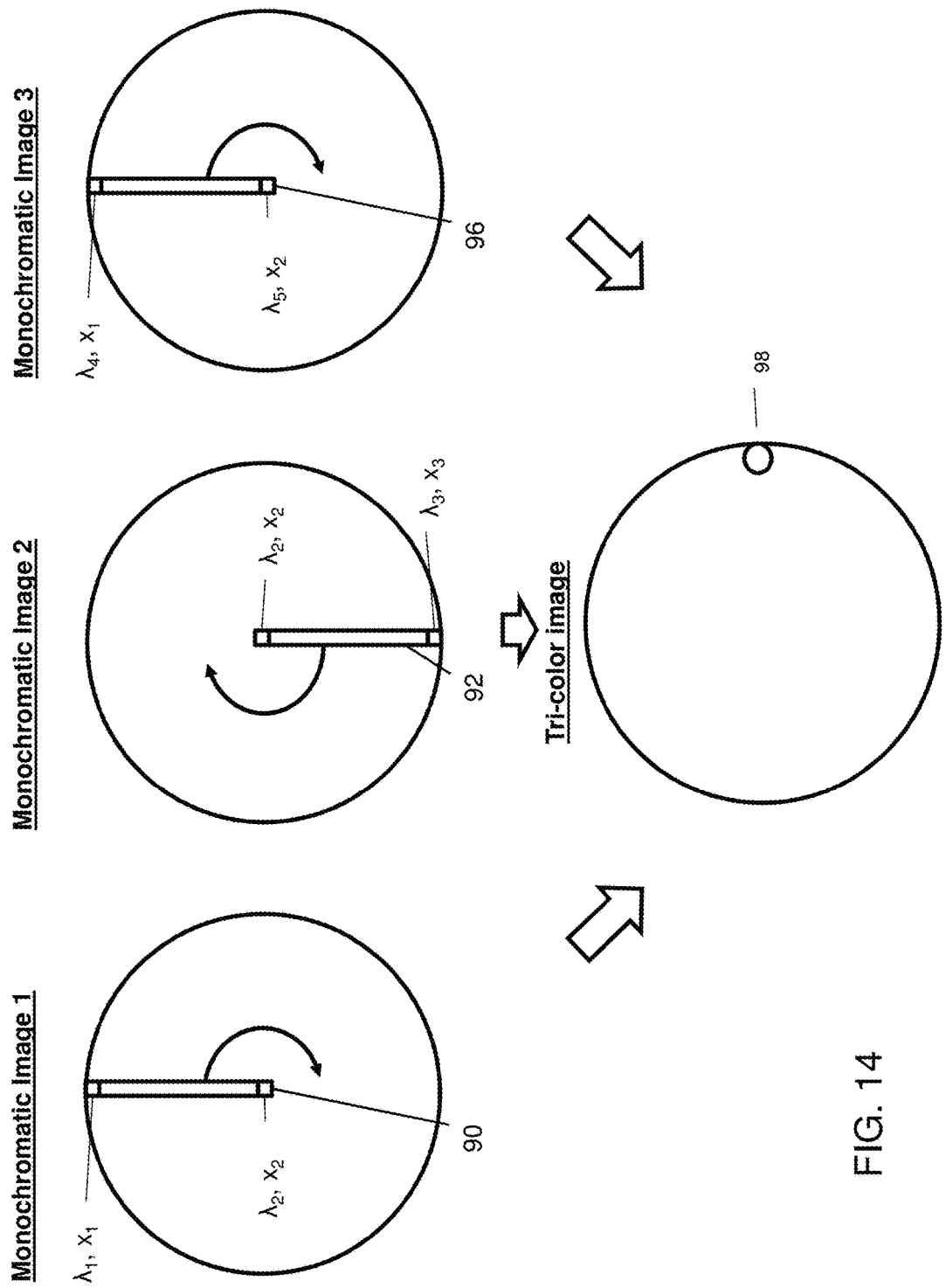
FIG. 14 a set of illustrations of the tri-color images that can be obtained from three monochromatic images by the SEE probe according to various exemplary embodiments of the present disclosure.

FIG. 14 shows set of illustrations of the tri-color images that can be obtained from three monochromatic images by the SEE probe according still further exemplary embodiment of the present disclosure. For example, a monochromatic image can be obtained by scanning the first spectrally-encoded line 90, which can correspond to the shorter half of the working spectrum. Another monochromatic image can be obtained by scanning the second spectrally-encoded line 92, which can correspond to the longer half of the working spectrum. Yet another monochromatic image can be obtained by scanning a third spectrally-encoded line 96. The monochromatic images can be combined to generate a tri-color image, such as a RGB-color image. This is shown in the lower part of FIG. 14, where each point on the color image are imaged by three wavelengths of the light, as exemplified by point 98, which was imaged by the light at the wavelengths $\lambda_1$, $\lambda_3$, and $\lambda_4$.

In other exemplary embodiments, two, three, or four monochromatic images can be formed and combined to generate or otherwise form a multi-color image (e.g., by a specifically programmed and configured computer). Thus, a two-tone image can be provided and or generated to, for example, distinguish between blood and tissue, or a three-tone image can be provided to create a full color image.

Figure 15:
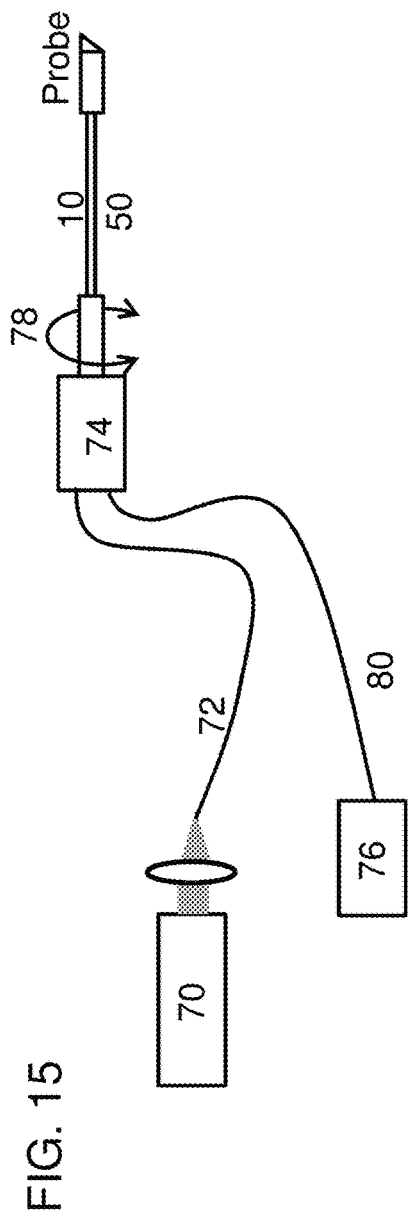
FIG. 15 is a diagram of the SEE apparatus according to an exemplary embodiment of the present disclosure.

A system to acquire the image from the SEE probe according to an exemplary embodiment of the present disclosure is shown in a diagram of FIG. 15. For example, a light source 70 outputs light of broadband spectrum (or other electro-magnetic radiation). The range of the wavelength can be within the visible region, which is from 400 nm thorough 800 nm. However, other wavelengths may also be used. In the exemplary imaging system, the light can be directly guided or otherwise provided into a fiber 72, which can be called an illumination fiber. The illumination fiber 72 can be connected to a junction 74, and further guided to (and/or associated with) another illumination fiber 10. At the end of the illumination fiber 10, the SEE exemplary probe can be attached. The light scattered back from the object (e.g., tissue) can be collected by a detection fiber 50. The detection fiber 50 can be connected to another detection fiber 8o by the junction 74. The detection fiber 80 can be connected to a detector 76 in which the intensity of selected wavelength can be detected. This exemplary function can be performed by, e.g., a spectrometer. For example, by mechanically scanning the probe perpendicular to the diffraction direction via a mechanical scan unit 78, it is possible obtain a two-dimensional image of the object. The mechanical scan can be performed by, e.g., Galvo scanner or motor to rotate the probe together with the illumination fiber 10 and the detection fiber 50.

In some exemplary embodiments, instead of guiding the broadband light into the illumination fiber 72, the light can first be dispersed to predetermined wavelength(s) $\lambda_1$, $\lambda_2$, ..., $\lambda_N$. For example, the light with the wavelength $\lambda i$ ($1 \le i \le N$) can be input into the illumination fiber 72. The input light is provided through the junction 74, illumination fiber 10, probe, detection fiber 50, junction 74, defection fiber 80, and the detector 76. Optionally, the detector 76 can be or include a simple light intensity detector such as photodetector because the input light has a wavelength of $\lambda i$. By changing i from 1 to N, it is possible to obtain the one-dimensional line image. By mechanically scanning the line, it is possible to acquire the two-dimensional image of the object.

One role of the optional junction 74 can be to make the probe, including the illumination fiber 10 and the detection fiber 50, detachable. With this exemplary function, the probe can be disposable to thereby being a sanitary probe to be inserted into a human body.

Various exemplary SEE probes as described and shown herein can deflect light along the reference axis, and facilitate forward viewing. The exemplary probe may be held stationary or it may be rotated, where the rotation of the probe is particularly useful for acquiring a two-dimensional front-view image as well as a color image.

For example, since the detection fiber 50 can be attached to the front-view type SEE probe, continuous rotation of the probe can cause the illumination fiber and the detection to become tangled. Therefore, in some exemplary embodiments, it is possible that the probe can be rotated, e.g., +/− approximately 360 degrees back and forth. In other exemplary embodiments, the exemplary probe can be rotated +/− approximately 180 degrees back and forth. In further exemplary embodiments, other degrees of rotation can be used, such as, e.g., 90 degrees or 270 degrees.

According to various exemplary embodiments, multi-cladding fiber can be utilize. Multi-cladding fiber can act as if it has different core diameters depending on a light propagating direction. Thus, such multi-cladding fiber can be used as the illumination fiber and the detection fiber. If the multi-cladding fiber is connected to a "rotary junction," continuous rotation of the probe can be performed.

Figure 16:
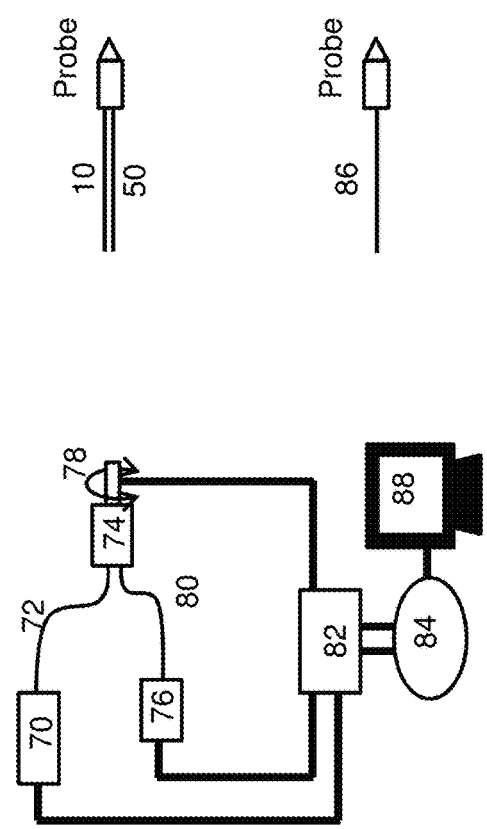
FIG. 16 is a diagram of an exemplary embodiment of an imaging apparatus using an exemplary embodiment of the front-view SEE probe.

FIG. 16 shows a diagram the imaging system according to another exemplary embodiment of the present disclosure. This exemplary imaging system can be used with, for example, the exemplary probes as described in various exemplary embodiments herein. The exemplary front-view SEE probes as described herein are categorized into two exemplary types. One type can use an illumination fiber and a detection fiber. The other type can use, e.g., only one fiber, which may be a multi-cladding fiber. Either one of the two types can be used in the exemplary imaging system shown in FIG. 16.

For example, to operate the imaging system of FIG. 16, a user (e.g., a doctor, nurse, or technician) can connect the exemplary front-view SEE probe to the junction 74. When the front-view SEE probe is connected to the junction 74, a computer unit/arrangement 82 can be programmed and configured to specifically detect and/or determine which of the two front-view SEE probes is connected, and can store the information into computer memory. The computer unit/arrangement 82 can include a central processing unit, memory, input/output interface, and data storage. In the data storage, software which configures the central processing unit to perform the determinations and various functions for the user to operate the imaging system can be pre-installed.

In an exemplary operation, the user can placed the exemplary front-view SEE probe into a sheath (not shown in FIG. 17), and then can insert such arrangement/configuration into a predetermined position of a human body. The sheath alone may be inserted into the human body in advance, and it is possible to insert the front-view SEE probe into the sheath. The exemplary probe can be used to observe inside human body and works as endoscope such as arthroscopy, vascular endoscope and so on.

A command can be transmitted to the computer unit/arrangement 82 via a user interface unit/arrangement 84. A touch panel screen can be includes as part of the user interface unit/arrangement 84, but key board, mouse, joystick, ball controller, and foot pedal can also be included with the user interface unit/arrangement 84. The user can cause a command to be initiated to observe inside the human body through the exemplary front-view SEE probe using the user interface unit 84. For example, when the user inputs a command, the command is transmitted to the central processing unit for execution thereby.

Both line scans and point scans can be used. For a line scan, when the computer unit/arrangement 82 received a command to observe inside the human body, the computer unit/arrangement 82 can be configured and specifically caused to send a signal to the light source 70. The light source 70 can be or include a super continuous laser that can realize a broadband emission or an arc lamp. For example, the source can provide radiations with wavelength that range from 400 nm through 800 nm continuously, however, other ranges are also contemplated. Once the light source 70 received the signal from the central processing unit, it can generate broadband light (or other radiation), which can be coupled into the illumination fiber 72.

The broadband light propagates into the illumination fiber 72, and reaches the junction 74. If the exemplary front-view SEE probe has an illumination fiber and a detection fiber, the light guided by the illumination fiber 72 can be connected to another illumination fiber 10. If the front-view SEE probe uses only a multi-cladding fiber, the light guided by the illumination fiber 72 can be connected to the multi-cladding fiber 86 such that only the core of the multi-cladding fiber guides the input light. The light is provided through the probe, and illuminates the object. The scattered light from the object can be collected by the probe.

If the front-view SEE probe has an illumination fiber 10 and a detection fiber 50, the scattered light goes into the detection fiber 50, which is connected to the detection fiber 80 at the junction 74. If the front-view SEE probe has only multi-cladding fiber, the scattered light may be designed to propagate in the inner cladding and the propagated light is coupled into the detection fiber 80 at the junction 74.

The detection fiber 50 can relay the light to the detector 76. The detector, such as a spectrometer, 76 can measure the intensity at predetermined wavelengths. The detected intensities can be acquired by the computer unit/arrangement 82 and optionally stored in memory thereof.

The computer unit/arrangement 82 can be programmed to apply exemplary image processing such as noise reduction, coordinate distortion correction, contrast enhancement and so on. After or even during the image processing is performed, the data can be transmitted from the computer unit/arrangement 82 to a display 88. In some exemplary embodiments, a liquid crystal display can be the display 88. The display 88 can display, for example, the image obtained by the line scan according to various exemplary embodiments of the present disclosure. The display 88 can also display other information than the image, such as the date of observation, what part of the human body is observed, the patient's name, operator's name and so on.

According to certain exemplary embodiments of the use of the SEE probe as described herein, the computer unit/arrangement 82 can then transmit another command to the mechanical scan unit/arrangement 78. With this command, the mechanical scan unit 78 is caused by the computer unit/arrangement 82 to rotate the exemplary front-view SEE probe by predetermined amount 60 around the reference axis. After the rotation, the line scan can be considered to be completed, the image data can be sent to the display 88, to be displayed (i.e., with the information regarding the rotation by 60). Repeating this step can provide a two-dimensional front-view image.

In some exemplary embodiments, where the front-view SEE probe has the illumination fiber 10 and the detection fiber 50, The computer unit/arrangement 82 may be configured and programmed to send a command such that the rotation direction flips after the sum of the absolute value of accumulation angle is more than 360 degrees (or 180 degrees, etc.). If the exemplary front-view SEE probe has only multi-cladding fiber, the computer unit/arrangement 82 can send a command to keep rotating the probe. Maintaining the rotation of the front-view SEE probe can have some advantages, including, e.g., reduces reduction of the rotation lag. For example, rotation angles of the mechanical scan unit/arrangement 78 and the front-view SEE probe can differ because the probe may not be perfectly rigid. When, the exemplary probe is rotated back and forth, the difference may not be constant over the time. However, when the probe is consistently rotated, the rotation lag can be nearly constant. Thus, the two-dimensional image has less distortion.

If the exemplary front-view SEE probe is rotated by 360·n degrees per second, the frame rate can be n frames per second. In some exemplary embodiments, n can be more than 30, more than 45, or more than 60. Thus, in such exemplary manner, it is possible to obtain real-time two-dimensional front view using the exemplary embodiments of the probe according to the present disclosure.

In other exemplary embodiments of the present disclosure, point scans can be used. When the computer unit/arrangement 82 received a command for observation, the computer unit/arrangement 82 can be programmed and configured to transmit a signal to the light source 70. The broadband light (or other radiation) can be dispersed, and a selected wavelength is coupled into the illumination fiber 72. The selected wavelength of the light can be determined by the computer unit/arrangement 82.

Similar to the exemplary line scan process, the scattered light from the object reaches the detector 76. In this exemplary embodiment, the detector 76 does not have to be a spectrometer. Instead, the detector 76 can be or include a point light intensity detector such as photo detector. The detected intensity is the intensity at one point of the line scan, which can be stored in the memory.

The computer unit/arrangement 82 can then change the selected wavelength of the source 79, and can be used to determine the intensity the light at another point of the line scan. By changing the wavelength in predetermined range (ex. from 400 nm to 800 nm), it is possible to obtain a line image. The computer unit/arrangement 82 can apply the image processing procedures to the obtained data and sends such data to be displayed on the display 88.

The computer unit/arrangement 82 can be programmed and configured to synchronize the selection of the wavelength of the light, the rotation of the mechanical scan unit 78, and the detection of the scattered light intensity to obtain a two-dimensional front-view image. The above-described exemplary data acquisition process can be called the point scan as described herein. With such exemplary point scan, it is possible to effectuate a cost reduction since a spectrometer does not have to be utilized.

According to certain exemplary embodiments of the present disclosure, the exemplary SEE probe can facilitate a view in a forward direction, which can add an additional value to various endoscopy systems. For example, the SEE probe according to various exemplary embodiments of the present disclosure can be useful in in vivo applications. The exemplary probe(s) can be configured for use in vivo, and, with a small size thereof, provide advantage over other large conventional probes that can require a more complex and invasive procedure for obtaining image data. Further, the exemplary SEE probe(s) as described herein can be useful for imaging in locations traditional endoscope cannot access such as in hands, fingers, feet, and other body areas where a traditional probe is too large to fit.

The exemplary embodiments are described with visible light, but the exemplary embodiments of the present disclosure are not limited to the use of visible light. For example, IR light or UV light may be used, as well as other electromagnetic radiations.

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

More specific examples will be explained in the following embodiments.

Example 1

An exemplary SEE probe according to an exemplary embodiment of the present disclosure with a light reflection component is shown in FIG. 4A. For simplicity, the insert 17 can be removed. For the light focusing component 12, a GRIN lens can be used. The fiber 10 is directly spliced to the GRIN lens' center. An approximate refractive index distribution of the GRIN lens can be written as $$N(r)=N_o(1-A/2*r^2),$$ (Eq. 2)

where r is the radial distance from the center of the GRIN lens. Commercially available GRIN lenses can have $N_o=1.61$ and $A=0.1781$ at 550 nm wavelength and such GRIN lens in used in the following. The length of the GRIN lens can be set to 4.0 mm. For the spacer 14, commercially available glass which has a refractive index of 1.5181 at 550 nm wavelength is used.

The light reflection component 13 can be formed by polishing the spacer 14. The angle between the polished surface and the reference axis can be set to about or exactly 37.5 degrees. The grating can have a period of about or exactly 550 nm, which can be formed into the surface of the spacer 14. The angle between the grating and the reference axis can also be about or exactly 37.5 degrees. The light blocking component 11 can block the light coming into half bottom of the GRIN lens.

Ray tracing was done with the wavelengths of 450, 550, 650, and 750 nm. The above parameters were chosen such that the light with a wavelength of 750 nm was deflected along the reference axis. For light with a targeted wavelength to be deflected toward the reference axis, the following equation should be satisfied $$n1\sin(\pi/2-\theta1-\theta g-2\theta m)-n2\sin(\pi/2-\theta g)=\lambda s/\Lambda$$ (Eq. 3)

where:
- n1: Refractive index of the grating
- n2: Refractive index of the material after grating (ex. air)
- θ1: angle of a ray from the reference axis before hitting the light reflection component (θ1<0 if going downward)
- θm: angle between the surface of light reflection component and the reference axis
- θg: angle between the surface of light reflection component and the reference axis
- λs: targeted wavelength
- Λ: the pitch of the grating The light with the wavelength of about or exactly 750 nm may be deflected along the reference axis because it is the parameters are chosen such that the wavelength of about or exactly 750 nm approximately satisfies Eq. 3.

A two-dimensional image can be obtained by rotating this probe such as by using the process disclosed herein.

Example 2

A combination of a mirror and grating was used to realize spectrally dispersed light to be directed toward the optical axis of the fiber. The schematic diagram sof the exemplary embodiments of the probe are shown in FIGS. 10A-10C.

For example, the mirror type front-view SEE probe can have a mirror at the tip of the probe. The light transmitted through the GRIN lens hits the mirror. The reflected light goes into the grating. In this exemplary way, the light is deflected parallel to the optical axis (z-direction).

As shown in FIG. 10A, to avoid the light that directly hit the grating without reflection by the mirror, the fiber can be offset. In this example, the mirror is at about or exactly 38° and the grating is at about or exactly 40° with a pitch of about or exactly 450 nm. The fiber can be offset 0.11 mm. In FIG. 10B, a light absorber can be added where the light absorber blocks light propagating into the grating but not into the mirror. The exemplary probe shown in FIG. 10B is designed so that the inclination of the mirror plane is the same angle as the inclination of the grating. This can simplify the fabrication of the distal probe. FIG. 10C shows the exemplary probe that is designed with a mirror at about or exactly 38°, a grating at about or exactly 45°, and a pitch of about or exactly 450 nm.

Example 3

Examples having variations of the light absorber can also be utilized. For example, as shown in FIG. 9A, the bottom part of the GRIN lens is absent. The bottom half can be removed, for example, by polishing or cutting away the half. Considering the balance of weight or moment when the probe is rotated, the detection fiber 10 can be attached to the removed space, as shown in FIG. 9C (with, e.g., the fiber 50), which can also have the advantage of reducing the total probe head volume. The solid portion illustrated in FIGS. 9A and 9C can be made by cutting a slit on the GRIN lens and filling with light absorbing material such as black epoxy, or any opaque material.

By designing the angle of reflection to be larger than the critical angle of refraction, the mirror can be formed by simply polishing the surface by use of the total internal reflection. Therefore, coating the surface would not be needed. Further, e.g., the light with longer wavelength can be diffracted closer to z-direction.

As used herein, the term substantially, such as light propagating substantially parallel or, for example, light having substantially similar angles, means that the difference in angle is less than 15°, or more particularly less than 10°, or more particularly less than 5°, or more particularly less than 3°, or more particularly less than 2°, or more particularly less than 1°.

The foregoing merely illustrates the principles of the disclosure. Various modifications and alterations to the described exemplary embodiments will be apparent to those skilled in the art in view of the teachings herein. Indeed, the arrangements, systems and methods according to the exemplary embodiments of the present disclosure can be used with any SEE system or other imaging systems, and for example with those described in U.S. Pat. Nos. 7,843,572, 8,145,018, 6,341,036, 7,796,270 and U.S. Patent Application Nos. 2008/0013960 and 2011/0237892, the disclosures of which are incorporated by reference herein in their entireties. It will thus be appreciated that those skilled in the art will be able to devise numerous systems, arrangements and methods which, although not explicitly shown or described herein, embody the principles of the disclosure and are thus within the spirit and scope of the present disclosure. In addition, to the extent that the prior art knowledge has not been explicitly incorporated by reference herein above, it is explicitly being incorporated herein in its entirety. All publications referenced herein above are incorporated herein by reference in their entireties.

The following non-limiting list of references is provided.
C. Pitris, B. E. Bouma, M. Shiskov, G. J. Tearney, OPTICS EXPRESS Vol. 11120-124 (2003)
M. Shishkov, G. J. Tearney, B. E. Bouma, D. Yelin, N. Iftimia, U.S. Pat. No. 8,145,018
D. Yelin, I. Rizvi, W. M. White, J. T. Motz, T. Hasan, B. E. Bouma and G. J. Tearney, "Three-dimensional miniature endoscopy," Nature Vol. 443, 765-765 (2006).

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A probe for forward viewing comprising:
   a light guiding component;
   a light focusing component;
   a light reflecting component; and
   a grating component;
   wherein the probe has a probe optical axis that is defined as extending along the direction of propagation of a light provided from the light guiding component through the light focusing component,
   wherein, from a proximal end of the probe in the direction of the probe optical axis, the light focusing component is provided after the light guiding component, the light reflecting component is provided after the light focusing component, and the grating component is provided after the light reflecting component, and
   wherein at least one of the light reflecting component and the grating component is positioned at an angle with respect to the probe optical axis such that, light reflected by the light reflecting component is incident on the grating component not parallel to the probe optical axis and when the light is transmitted through the grating component, at least one diffracted light propagates directly in a forward direction from the grating component substantially parallel to the probe optical axis.

2. The probe according to claim 1,
   wherein the light reflecting component and the grating component are angled with respect to the probe optical axis such that, when the light is transmitted through the light guiding component, at least two diffracted lights propagate from the grating component having a first and second wavelength, respectively,
   wherein the first wavelength being smaller than the second wavelength, and wherein the diffracted light having the second wavelength propagates more parallel to the probe optical axis than the diffracted light having the first wavelength.

3. The probe according to claim 1,
   wherein the light reflecting component and the grating component are angled with respect to the probe optical axis such that, when the light is transmitted through the light guiding component, at least two diffracted lights propagate from the grating component having the first and second wavelength, respectively,
   wherein the first wavelength being smaller than the second wavelength, and wherein, the diffracted light having the first wavelength propagates more parallel to the probe optical axis than the diffracted light having the second wavelength.

4. The probe according to claim 1, wherein the light reflecting component is configured and positioned to accept the light from the light guiding component at an incident angle that exceeds a predetermined angle.

5. The probe according to claim 1, wherein the at least one diffracted light has an angle of less than 1° from the probe optical axis.

6. The probe according to claim 1, wherein the light reflecting component comprises a mirror.

7. The probe according to claim 1, wherein a light guiding component comprises an optical fiber with multiple cladding.

8. The probe according to claim 1, wherein the light focusing component comprises a gradient index (GRIN) lens.

9. The probe according to claim 8, wherein a longitudinal portion of the gradient index lens has a removed section.

10. The probe according to claim 8, wherein the light focusing component further comprises a spacer.

11. The probe according to claim 1, wherein the light reflecting component and the grating component are integrally combined as a single element.

12. The probe according to claim 1, further comprising a light blocking component, positioned between the light focusing component and the light reflecting component in the direction along the probe optical axis, the light blocking component is configured to at least partially block the light exiting the light focusing component.

13. The probe according to claim 1, wherein the light guiding component is optically connected to the light focusing component at an off-center position.

14. The probe according to claim 1, wherein the probe is an endoscopy probe that is attached to a rotary junction.

15. The probe of claim 1, further comprising a sheath enclosing at least one portion of at least one of the light guiding component, the light focusing component, the light reflecting component, or the grating component.

16. The probe according to claim 1,
wherein, when the light is transmitted through the light guiding component, at least two additional diffracted lights propagate from the grating component,
wherein the at least two additional diffracted lights propagate at substantially the same angle with respect to the probe optical axis and on opposite sides of the probe optical axis.

17. The probe according to claim 16, wherein, when the light is transmitted through the light guiding component, the diffracted lights having a first order are arranged substantially symmetrically over the probe optical axis.

18. The probe according to claim 1,
wherein, when the light comprising a wavelength ranging from a first wavelength to a second wavelength is transmitted through the light guiding component, a propagation angle of the light provided at the second wavelength diffracted at a first order with respect to the probe optical axis is substantially similar and on an opposite side of the probe optical axis as compared to a propagation angle of the light provided at the first wavelength diffracted at a first order.

19. The probe according to claim 18, wherein the propagation angle of the light provided at a first wavelength diffracted at the first order is substantially similar to a propagation angle of the light provided at a second wavelength diffracted at a different order.

20. An imaging apparatus comprising the probe of claim 1, a light intensity detector receiving at least one electromagnetic radiation from the probe, and a broadband light source providing the light to the probe.

21. The probe according to claim 1, wherein the at least one diffracted light propagating directly in a forward direction from the grating component is at a position offset from and substantially parallel to the probe optical axis.

22. The probe according to claim 1,
wherein the light reflecting component is positioned with a reflecting surface at a first angle with respect to the probe optical axis, and the grating component is positioned at a second angle different from the first angle with respect to the optical axis.

23. The probe according to claim 1,
wherein both the reflecting surface of the light reflecting component and the grating component are positioned at a same angle with respect to the probe optical axis.

24. The probe according to claim 1,
wherein the grating component is a transmissive grating.

25. The probe according to claim 24, wherein, for a light with a targeted wavelength λs to be deflected toward the probe optical axis, the transmissive grating satisfies the following equation $$n1 \sin(\pi/2 - \theta1 - \theta g - 2\theta m) - n2 \sin(\pi/2 - \theta g) = \lambda s/\Lambda \quad \text{(Eq. 3)}$$

where:
n1 is the refractive index of the grating
n2 is the refractive index of the material after grating,
θ1 is the angle of a ray of light with respect to the probe optical axis before hitting the light reflection component,
θm is the angle between the surface of the light reflection component and the probe optical axis,
θg is the angle between the surface of the grating component and the probe optical axis,
λs is the targeted wavelength, and
Λ is the pitch of the transmissive grating.

26. A method for generation a color image of at least one sample, comprising:
providing a probe for forward viewing comprising:
a light guiding component,
a light focusing component,
a light reflecting component, and
a grating component,
wherein the probe has a probe optical axis that is defined as extending along the direction of propagation of a light provided from the light guiding component through the light focusing component,
wherein, from a proximal end of the probe along the direction of the probe optical axis, the light focusing component in provided after the light guiding component, the light reflecting component is provided after the light focusing component, and the grating component is provided after the light reflecting component, and
wherein at least one of the light reflecting component and the grating component is positioned at an angle with respect to the probe optical axis such that, light reflected by the light reflecting component is incident on the grating component not parallel to the probe optical axis and when the light is transmitted through the grating component, at least one diffracted light propagates directly in a forward direction from the grating component substantially parallel to the probe optical axis,
rotating the probe around the probe optical axis;
obtaining at least two images of the at least one sample per rotation; and
with a computer, combining the at least two images to generate the color image.

27. The method of claim 26, wherein the combining comprises combining data from an area of the at least one sample which is a substantially symmetrical cone around the probe optical axis.

28. The method of claim 26, wherein the at least two images include at least three images that are obtained per the rotation of the probe.

* * * * *